United States Patent
Senter et al.

(10) Patent No.: US 10,342,811 B2
(45) Date of Patent: *Jul. 9, 2019

(54) METHODS OF INHIBITION OF PROTEIN FUCOSYLATION IN VIVO USING FUCOSE ANALOGS

(71) Applicant: Seattle Genetics, Inc., Bothell, WA (US)

(72) Inventors: Peter Senter, Seattle, WA (US); Stephen Alley, Seattle, WA (US); Dennis Benjamin, Redmond, WA (US)

(73) Assignee: Seattle Genetics, Inc., Bothell, WA (US)

(*) Notice: Subject to any disclaimer, the term of this patent is extended or adjusted under 35 U.S.C. 154(b) by 114 days.

This patent is subject to a terminal disclaimer.

(21) Appl. No.: 15/299,894

(22) Filed: Oct. 21, 2016

(65) Prior Publication Data
US 2017/0035790 A1    Feb. 9, 2017

Related U.S. Application Data

(63) Continuation of application No. 13/814,083, filed as application No. PCT/US2011/046857 on Aug. 5, 2011, now Pat. No. 9,504,702.

(60) Provisional application No. 61/371,116, filed on Aug. 5, 2010.

(51) Int. Cl.
| | |
|---|---|
| *A61K 9/00* | (2006.01) |
| *A61K 39/00* | (2006.01) |
| *A61K 45/06* | (2006.01) |
| *C07K 16/00* | (2006.01) |
| *C07K 16/18* | (2006.01) |
| *A61K 31/7004* | (2006.01) |
| *A61K 31/7024* | (2006.01) |
| *A61K 31/7042* | (2006.01) |
| *A61K 31/706* | (2006.01) |
| *A61K 31/7048* | (2006.01) |

(52) U.S. Cl.
CPC ........ *A61K 31/7004* (2013.01); *A61K 9/0053* (2013.01); *A61K 31/706* (2013.01); *A61K 31/7024* (2013.01); *A61K 31/7042* (2013.01); *A61K 31/7048* (2013.01); *A61K 39/0011* (2013.01); *A61K 45/06* (2013.01); *C07K 16/00* (2013.01); *C07K 16/18* (2013.01); *A61K 2039/5152* (2013.01); *A61K 2039/545* (2013.01); *C07K 2317/41* (2013.01); *Y02A 50/386* (2018.01); *Y02A 50/388* (2018.01); *Y02A 50/401* (2018.01); *Y02A 50/403* (2018.01); *Y02A 50/412* (2018.01); *Y02A 50/484* (2018.01)

(58) Field of Classification Search
None
See application file for complete search history.

(56) References Cited

U.S. PATENT DOCUMENTS

| | | |
|---|---|---|
| 4,407,817 A | 10/1983 | Chan |
| 5,034,517 A | 7/1991 | Umezawa et al. |
| 5,210,078 A | 5/1993 | Toyokuni et al. |
| 5,374,746 A | 12/1994 | Ok et al. |
| 5,461,143 A | 10/1995 | Wong et al. |
| 5,595,976 A | 1/1997 | Billington et al. |
| 5,770,407 A | 6/1998 | Wong et al. |
| 5,945,404 A | 8/1999 | Sugai et al. |
| 6,075,134 A | 6/2000 | Bertozzi et al. |
| 6,143,724 A | 11/2000 | Ohira |
| 6,458,937 B1 | 10/2002 | Bertozzi et al. |
| 6,489,302 B1 | 12/2002 | Wiessler et al. |
| 6,713,287 B1 | 3/2004 | Wong |
| 6,936,701 B2 | 8/2005 | Bertozzi et al. |
| 6,979,675 B2 | 12/2005 | Tidmarsh |
| 7,160,865 B2 | 1/2007 | Lampidis et al. |
| 7,214,660 B2 | 5/2007 | DeFrees et al. |
| 7,265,084 B2 | 9/2007 | DeFrees et al. |
| 7,335,500 B2 | 2/2008 | Wong et al. |
| 7,351,408 B2 | 4/2008 | Bertozzi et al. |
| 7,968,687 B2 | 6/2011 | McDonagh et al. |
| 8,163,551 B2 | 4/2012 | Alley et al. |
| 8,242,167 B2 | 8/2012 | Lampidis et al. |
| 8,278,349 B2 | 10/2012 | Kloog et al. |
| 8,299,033 B2 | 10/2012 | Priebe |
| 8,633,021 B2 | 1/2014 | Xia et al. |
| 8,993,326 B2 | 3/2015 | Alley et al. |
| 2004/0132140 A1 | 7/2004 | Satoh et al. |
| 2005/0043250 A1 | 2/2005 | Lampidis et al. |
| 2006/0009400 A1 | 1/2006 | Eckhaerdt et al. |
| 2006/0246456 A1 | 11/2006 | Tsuchiya et al. |

(Continued)

FOREIGN PATENT DOCUMENTS

| | | |
|---|---|---|
| EP | 1 676 910 A1 | 7/2006 |
| WO | WO 1989/010929 | 11/1989 |

(Continued)

OTHER PUBLICATIONS

Geng, F. et al., Cell Research, "The expression of core fucosylated E-cadherin in cancer cells and lung cancer patients: prognostic implications", 2004, vol. 14, No. 5, pp. 423-433 (Year: 2004).*
Miyoshi, E. et al., Proteonomics, "Fucosylated haptoglobin is a novel marker for pancreatic cancer: Detailed analyses of oligosaccharide structures", 2008, vol. 8, pp. 3257-3262 (Year: 2008).*
Moriwaki, K. et al., World Journal of Hepatology, "Fucosylation and gastrointestinal cancer", 2010, vol. 2, No. 4, pp. 151-161 (Year: 2010).*

(Continued)

*Primary Examiner* — Shaojia A Jiang
*Assistant Examiner* — Bahar Craigo
(74) *Attorney, Agent, or Firm* — Seattle Genetics, Inc.

(57) ABSTRACT

The invention provides methods and compositions for the inhibition of fucosylation of proteins, including antibodies, in vivo by administration of a fucose analog.

20 Claims, 10 Drawing Sheets

(56) References Cited

U.S. PATENT DOCUMENTS

| | | |
|---|---|---|
| 2007/0190597 A1 | 8/2007 | Agnew et al. |
| 2007/0249014 A1 | 10/2007 | Agnew et al. |
| 2008/0026943 A1 | 1/2008 | Fischer et al. |
| 2008/0166756 A1 | 7/2008 | Tsuchiya et al. |
| 2009/0305972 A1 | 12/2009 | Chahal et al. |
| 2010/0130434 A1 | 5/2010 | Priebe et al. |
| 2011/0003338 A1 | 1/2011 | Bayer et al. |
| 2011/0003758 A1 | 1/2011 | Priebe et al. |
| 2012/0183997 A1 | 7/2012 | Alley et al. |
| 2012/0202762 A1 | 8/2012 | Magnani |
| 2012/0276108 A1 | 11/2012 | Priebe |
| 2015/0238509 A1 | 8/2015 | Benjamin et al. |

FOREIGN PATENT DOCUMENTS

| | | |
|---|---|---|
| WO | WO 1992/019632 | 11/1992 |
| WO | WO 1998/018805 | 5/1998 |
| WO | WO 98/25940 A1 | 6/1998 |
| WO | WO 1998/054365 | 12/1998 |
| WO | WO 2004/033651 | 4/2004 |
| WO | WO 2004/091499 A2 | 10/2004 |
| WO | WO 2004/099231 | 11/2004 |
| WO | WO 2005/061523 | 7/2005 |
| WO | WO 2007/048122 A2 | 4/2007 |
| WO | WO 2007/081031 | 7/2007 |
| WO | WO 2007/111952 A2 | 10/2007 |
| WO | WO 2008/052030 | 5/2008 |
| WO | WO 2008/052030 A2 | 5/2008 |
| WO | WO 2009/108926 | 9/2009 |
| WO | WO2009/135181 A2 | 11/2009 |
| WO | WO 2009/143078 A2 | 11/2009 |
| WO | WO 2010/005735 | 1/2010 |
| WO | WO 2009/143515 | 2/2010 |
| WO | WO 2010/111713 | 4/2011 |
| WO | WO 2011/137527 | 11/2011 |
| WO | WO 2011/137528 | 11/2011 |

OTHER PUBLICATIONS

Ortmann, M. et al., Virchows Archiv B Cell Pathology including Molecular Pathology, "Sialylated glycoconjugates in chromophobe cell renal carcinoma compared with other renal cell tumors", 1991, vol. 61, pp. 123-132 (Year: 1991).*

Schwartz, R. et al., International Journal of Cancer, "Glycoconjugates of Murine Tumor Lines with Different Metastatic Capacities. I. Differences in Fucos Utilization and in Glycoprotein Patterns", 1984, vol. 33, pp. 503-509 (Year: 1984).*

Zips, D. et al., In Vivo, "New Anticancer Agents: In Vitro and In Vivo Evaluation", 2005, vol. 19, pp. 1-8 (Year: 2005).*

Okeley, N. et al., Proceedings of the 103rd Annual Meeting of the American Association for Cancer Research; Mar. 31-Apr. 4, 2012; Chicago, IL. Philadelphia (PA): AACR; Cancer Res 2012;72(8 Suppl):Abstract nr 2945. doi:1538-7445.AM2012-2945 (Year: 2012).*

Albermann et al. "Preparative Synthesis of GDP-β-L-Fucose by Recombinant Enzymes From Enterobacterial Sources," Glycobiology 2000, vol. 10, No. 9, pp. 875-881.

Alton et al. "Direct Utilization of Mannose for Mammalian Glycoprotein Biosynthesis," Glycobiology 1998, vol. 8, No. 3, pp. 285-295.

Baisch et al. "Synthetic Potential of Cloned Fucosyl-Transferase III and VI," Bioorganic & Medicit:al Chemistry Letters 1997, vol. 7, No. 19, pp. 2447-2450.

Barbin, K. et al., "Influence of Variable N-Glycosylation on the Cytolytic Potential of Chimeric CD19 Antibodies," *J. Immunother.*, Mar./Apr. 2006, vol. 29, No. 2, pp. 122-133.

Baskin et al. "Bioorthogonal Click Chemistry: Covalent Labeling in Living Systems," QSAR Comb. Sci. 2007, vol. 26, No. 11-12, pp. 1211-1219.

Beacham et al. "Inhibition of Fucosyl Transferase and Fucosidase by a Rigid Bicyclic Mimic of α-L-Fucose," Tetrahedron Letters 1998, vol. 39, pp. 151-154.

Becker et al. "Fucose: Biosynthesis and Biological Function in Mammals," Glycobiology 2003, vol. 13, No. 7, pp. 41R-53R.

Braun et al. "Mechanism-Based Inhibition of Yeast a-Glucosidase and Human Pancreatic α-Amylase by a New Class of Inhibitors," The Journal of Biological Chemistry 1995, vol. 270, No. 45, pp. 26778-26781.

Brown et al. "Glycan Antagonists and Inhibitors: A Fount for Drug Discovery," Critical Reviews in Biochemistry and Molecular Biology 2007, vol. 42, pp. 481-515.

Burkart et al. "Chemo-Enzymatic Synthesis of Fluorinated Sugar Nucleotide: Useful Mechanistic Probes for Glycosyltransferases," Bioorganic & Medicinal Chemistry 2000, vol. 8 pp. 1937-1946.

Butters et al. "Molecular Requirements of Imino Sugars for the Selective Control of N-Linked Glycosylation and Glycosphingolipid Biosynthesis," Tetrahedron: Asymmetry 2000, vol. 11, pp. 113-124.

Cai et al. "Synthesis of Carbocyclic Analogs of Guanosine 5'-(.Beta.-I-Fucopyranosyl Diphosphate) (GDP-Fucose) as Potential Inhibitors of Fucosyltransferases," J. Org. Chem. 1992, vol. 57, pp. 6693-6696.

Calderón et al. "Structure/Activity Relationship of Carba- and C-Fucopyranosides as Inhibitors of an α1,6-Fucosyltransferase by Molecular Modeling and Kinetic Studies," Letters in Organic Chemistry 2005,vol. 2, pp. 247-251.

Clark et al. "Expression of Human α-L-Fucosyltransferase Gene Homologs in Monkey Kidney COS Cells and Modification of Potential Fucosyltransferase Acceptor Substrates by an Endogenous Glycosidase," Glycobiology 1999, vol. 9, No. 2, pp. 191-202.

Codelli et al. "Second-Generation Difluorinated Cyclooctynes for Copper-Free Click Chemistry," J. Am. Chem. Soc. 2008, vol. 130, pp. 11486-11493.

Compain et al. "Carbohydrate Mimetics-Based Glycosyltransferase Inhibitors," Bioorganic & Medicinal Chemistry 2001, vol. 9, pp. 3077-3092.

Compain et al. "Design, Synthesis and Biological Evaluation of Iminosugar-Based Glycosyltransferase Inhibitors," Current Topics in Medicinal Chemistry 2003, vol. 3, pp. 541-560.

Derossi et al. "Ablation of Mouse Phosphomannose Isomerase (Mpi) Causes Mannose 6Phosphate Accumulation, Toxicity, and Embryonic Lethality," The Journal of Biological Chemistry 2006, vol. 281, No. 9, pp. 5916-5927.

Ferrara et al. "The Carbohydrate at FcγRIIIa Asn-162—An Element Required for High Affinity Binding to Non-Fucosylated IgG Glycoforms," The Journal of Biological Chemistry 2006, vol. 281, No. 8, pp. 5032-5036.

Fessner et al. "Enzymes in Organic Synthesis, 15 Short Enzymatic Synthesis of L-Fucose Analogs," Eur. J. Org. Chem. 2000, pp. 125-132.

Galan et al. "The design and Synthesis of a Selective Inhibitor of Fucosyltransferase VI," Org. Biomol. Chem. 2004, vol. 2, pp. 1376-1380.

Gamblin et al. "Glycoprotein Synthesis: An Update," Chem. Rev. 2009, vol. 109, pp. 131-163.

Gonzalez et al., "Fragmentation of carbohydrate anomeric alkoxy radicals: A mew synthesis of chiral 1-halo-1-iodo Alditois," Chemistry—A European Journal, 2003, vol. 9, No. 23, pp. 5800-05809.

Goon et al. "Metabolic Substrate Engineering as a Tool for Glycobiology," Journal of Carbohydrate Chemistry 2002, vol. 21, No. 7, pp. 943-977.

Gosselin et al. "A Continuous Spectrophotometric Assay for Glycosyltransferases," Analytical Biochemistry 1994, vol. 220, pp. 92-97.

Gross et al. "Inhibition of Protein N-Glycosylation by 2-Deoxy-2-Fluoro-D-Galactose," Biochem. J. 1992, vol. 285, pp. 821-826.

Grün et al. "Metabolism and Actions of 2-Deoxy-2-Fluoro-D-Galactose In Vivo," Eur. J. Biochem. 1990, vol. 190, pp. 11-19.

Hanson et al. "Probing Glycans With the Copper(I)-Catalyzed [3+2] Azide—Alkyne Cycloaddition," QSAR Comb. Sci. 2007, vol. 26, No. 11-12, pp. 1243-1252.

Hsu, T-L. et al. "Alkynyl sugar analogs for the labeling and visualization of glycoconjugates in cells," *PNAS*, Feb. 20, 2007, vol. 104, No. 8, pp. 2614-2619.

Ichikawa et al. "Chemical-Enzymatic Synthesis and Conformational Analysis of Sialyl Lewis x and Derivatives," J. Am. Chem. Soc. 1992, vol. 114, pp. 9283-9298.

(56) References Cited

OTHER PUBLICATIONS

Ihara et al. "Crystal Structure of Mammalian α1,6-fucosyltransferase, FUT8," Glycobiology 2007, vol. 17, No. 5, pp. 455-466.
Ihara et al. "Reaction Mechanism and Substrate Specificity for Nucleotide Sugar of Mammalian α1,6-Fucosyltransferase—A Large-Scale Preparation and Characterization of Recombinant Human FUT8," Glycobiology 2006, vol. 16, No. 4, pp. 333-342.
Iida et al. "Nonfucosylated Therapeutic IgG1 Antibody Can Evade the Inhibitory Effect of Serum Immunoglobulin G on Antibody-Dependent Cellular Cytotoxicity Through Its High Binding to FcγRIIIa," Clin Cancer Res 2006, vol. 12, No. 9, pp. 2879-2887.
Imai-Nishiya et al. "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnology 2007, vol. 7, p. 84.
International Search Report dated Nov. 25, 2009, for International Application No. PCT/US09/42610 filed on May 1, 2009, 4 pages.
Ishiwata et al. "6-[$^{18}$F] Fluoro-L-fucose: A Possible Tracer for Assessing Glycoconjugate Synthesis in Tumors with Positron Emission Tomography," J. Nucl. Med. 1990, vol. 31, pp. 1997-2003.
Jefferis "Glycosylation as a Strategy to Improve Antibody-Based Therapeutics," Nature Reviews, Drug Discovery 2009, vol. 8, pp. 227-234.
Jones et al. "Characterization of the Cellular Uptake and Metabolic Conversion of Acetylated N-Acetylmannosamine (ManNAc) Analogues to Sialic Acids," Biotechnology and Bioengineering 2004, vol. 85, No. 4, pp. 394-405.
Kanda et al. "Comparison of Biological Activity Among Nonfucosylated Therapeutic IgG1 Antibodies with Three Different N-Linked Fc Oligosaccharides: The High-Mannose, Hybrid, and Complex Types," Glycobiology 2006, vol. 17, No. 1, pp. 104-118.
Kanda et al. "Establishment of a GDP-Mannose 4,6-Dehydratase (GMD) Knockout Host Cell Line: A New Strategy for Generating Completely Non-Fucosylated Recombinant Therapeutics," Journal of Biotechnology 2007, vol. 130, pp. 300-310.
Kim et al. "Characterization of the Metabolic Flux and Apoptotic Effects of O-Hydroxyl- and N-Acyl-modified N-Acetylmannosamine Analogs in Jurkat Cells," The Journal of Biological Chemistry 2004, vol. 279, No. 18, Issue of Apr. 30, pp. 18342-18352.
Laughlin et al. "Imaging the Glycome," PNAS 2009, vol. 106, No. 1, pp. 12-17.
Laughlin et al. "Metabolic Labeling of Glycans with Azido Sugars and Subsequent Glycan-Profiling and Visualization via Staudinger Ligation," Nature Protocols 2007, vol. 2, No. 11, pp. 2930-2944.
Lee et al. "A Potent and Highly Selective Inhibitor of Human α-1,3-Fucosyltransferase via Click Chemistry," J. Am. Chem. Soc. 2003, vol. 125, pp. 9588-9589.
Lee et al. "Analogs of Cell Surface Carbohydrates. Synthesis of D-Galactose Derivatives Having an Ethynyl, Vinyl or Epoxy Residue at C-5," Carbohydrate Research 1988, vol. 176, pp. 59-72.
Lim et al. "Glycosylation Profiling of a Therapeutic Recombinant Monoclonal Antibody with Two N-Linked Glycosylation Sites Using Liquid Chromatography Coupled to a Hybrid Quadrupole Time-of-Flight Mass Spectrometer," Analytical Biochemistry 2008, vol. 375, pp. 163-172.
Luchansky et al. "Expanding the Diversity of Unnatural Cell-Surface Sialic Acids," ChemBioChem 2004, vol. 5, pp. 371-374.
Maeda et al. "Fret-Based Direct and Continuous Monitoring of Human Fucosyltransferases Activity: An Efficient synthesis of Versatile GDP-L-Fucose Derivatives from Abundant D-Galactose," Chem. Eur. J. 2008, vol. 14, 478-487.
Matsumura et al. "Carbohydrate Binding Specificity of a Fucose-specific Lectin From *Aspergillus oryzae*—A Novel Probe for Core Fucose," The Journal of Biological Chemistry 2007, vol. 282, No. 21, pp. 15700-15708.
May, Jr., et al. "Synthesis and Biological Activity of Potential Antimetabolites of L-Fucose," Journal of Medicinal Chemistry 1979, vol. 22, No. 8, pp. 971-976.

Mori et al. "Engineering Chinese Hamster Ovary Cells to Maximize Effector Function of Produced Antibodies Using FUT8 siRNA," Biotechnology and Bioengineering 2004, vol. 88, No. 7, pp. 901-908.
Mori et al. "Non-Fucosylated Therapeutic Antibodies: The Next Generation of Therapeutic Antibodies," Cytotechnology 2007, vol. 55, pp. 109-114.
Murray et al. "Mechanism of Human α-1,3-Fucosyltransferase V: Glycosidic Cleavage Occurs Prior to Nucleophilic Attack," Biochemistry 1997, vol. 36, pp. 823-831.
Niittymäki "GDP-L-Fucose: Synthesis and Role in Inflammation," Academic Dissertation 2007, Department of Bacteriology and Immunology, Haartman Institute and Biomedicum Helsinki and Division of Biochemistry, Department of Biological and Environmental Sciences, Faculty of Biosciences University of Helsinki and Glycoscience Graduate School.
Niittymaki et al. "Cloning and Expression of Murine Enzymes Involved in the Salvage Pathway of GDP-L-Fucose L-Fucokinase and GDP-L-Fucose Pyrophosphorylase," Eur. J. Biochem. 2004, vol. 271, pp. 78-86.
Norris et al. "Inhibition Kinetics of Carba- and Gfucosyl Analogues of GDP-Fucose Against Fucosyltransferase v: Implication for the Reaction Mechanism," Bioorganic & Medicinal Chemistry Letters 2004, vol. 14, pp. 571-573.
Okeley et al., "Development of orally active inhibitors of protein and cellular fucosylation," PNAS 2013, vol. 110(14):5404-5409.
Okeley et al., enhancement of antibody effector function activities through biochemical inhibition of fucosylation, Abstract No. 608, 2011.
Omasa et al. "Decrease in Antithrombin III Fucosylation by Expressing GDP-Fucose Transporter siRNA in Chinese Hamster Ovary Cells," Journal of Bioscience and Bioengineering 2008, vol. 106, No. 2, pp. 168-173.
Pan et al. "Castanospermine Inhibits the Processing of the Oligosaccharide Portion of the Influenza Viral Hemagglutinin," Biochemistry 1983, vol. 22, pp. 3975-3984.
Panneerselvam et al. "Human Fibroblasts Prefer Mannose over Glucose as a Source of Mannose for N-Glycosylation," The Journal of Biological Chemistry 1997, vol. 272, No. 37, pp. 23123-23129.
Papac et al. "A High-Throughput Microscale Method to Release N-Linked Oligosaccharides From Glycoproteins for Matrix-Assisted Laser Desorption/Ionization Time-of-Flight Mass Spectrometric Analysis," Glycobiology 1998, vol. 8, No. 5, pp. 445-454.
Park et al. "Characterization and Role of Fucose Mutarotase in Mammalian Cells," Glycobiology 2007, vol. 17, No. 9, pp. 955-962.
Park et al. "Chemical Tools for Functional Studies of Glycans," Chem. Soc. Rev. 2008, vol. 37, pp. 1579-1591.
Peipp et al. "Antibody Fucosylation Differentially Impacts Cytotoxicity Mediated by NK and PMN Effector Cells," wwwbloodjournal.org at University of Washington on Jun. 20, 2008.
Prescher et al., "Chemistry in Living Systems," Nature Chemical Biology 2005, vol. 1, No. 1, pp. 13-21.
Qiao et al. "Synergistic Inhibition of Human α-1,3-Fucosyltransferase V," J. Am. Chem. Soc. 1996, vol. 118, pp. 7653-7662.
Rabuka et al. "A Chemical Reporter Strategy to Probe Glycoprotein Fucosylation," J. Am. Chem. Soc. 2006, vol. 28, pp. 12078-12079.
Rillahan et al., "Global Metabolic Inhibitors of Sialyl- and Fucosyltransferases Remodel the Glycome," Nature Chem. Biol. 8:661-668, 2012.
Sampathkumar et al. "Metabolic Installation of Thiols into Sialic Acid Modulates Adhesion and Stem Cell Biology," Nature Chemical Biology 2006, vol. 2, No. 3, pp. 149-152.
136 . Sawa et al. "Glycoproteomic Probes for Fluorescent Imaging of Fucosylated Glycans In Vivo," PNAS 2006, vol. 103, No. 33, pp. 12371-12376.
Saxon et al. "Investigating Cellular Metabolism of Synthetic Azidosugars with the Staudinger Ligation," J. Am. Chem. Soc. 2002, vol. 124, pp. 14893-14902.
Schuster et al. "Improved Effector Functions of a Therapeutic Monoclonal Lewis Y-Specific Antibody by Glycoform Engineering," Cancer Res 2005, vol. 65, No. 17, pp. 7934-7941.

(56) References Cited

OTHER PUBLICATIONS

Shinkawa et al., "The absence of fucose but not the presence of galactose or bisecting N-acetylglucosamine of human IgG1 complex-type oligosaccharides shows the critical role of enhancing antibody-dependent cellular cytotoxicity," Journal of Biological Chemistry, 2003, vol. 278, No. 5, pp. 3466-3473og.
Stankova, J. et al., "Fucose-Activated Killer (FAK) Cells: Anomalous Killers With Augmented Cytotoxic Activity," *The Journal of Immunology*, Dec. 6, 1985, vol. 135, No. 6, pp. 3718-3728.
Sturla et al. "Expression, Purification and Characterization of GDP-D-Mannose 4,6-Dehydratase From *Escherichia coli*," FEBS Letters 1997, vol. 412, pp. 126-130.
Sufrin et al. "Halogenated L-Fucose and D-Galactose Analogs: Synthesis and Metabolic Effects," J. Med. Chem. 1980, vol. 23, No. 2, pp. 143-149.
Supplementary European Search Report, dated Oct. 2, 2012, EP application No. 09 73 9983, 2 pages.
Takahashi et al. "A Sequence Motif Involved in the Donor Substrate Binding by α1,6-fucosyltransferase: the Role of the Conserved Residues," Glycobiology 2000, vol. 10, No. 5, pp. 503-510.
Tanaka et al. "Design and Synthesis of Peptide Mimetics of GDP-Fucose: Targeting Inhibitors of Fucosyltransferases," Synlett 2004, No. 2, pp. 243-246.
Tarling et al. "Identification of the Catalytic Nucleophile of the Family 29 α-L-Fucosidase from *Thermotoga maritima* through Trapping of a Covalent Glycosyl-Enzyme Intermediate and Mutagenesis," The Journal of Biological Chemistry 2003, vol. 278, No. 48, pp. 47394-47399.
Ulgar et al. "New N-Alkylsulfonamides and Alkyl Sulfonates Derived From 6-C-Sulfosugars," Tetrahedron 2002, vol. 58, pp. 7967-7973.
Vocadlo et al. "A Chemical Approach for Identifying O-GlcNAc-Modified Proteins in Cells," PNAS 2003, vol. 100, No. 16, pp. 9116-9121.
Vogel et al. "Galacturonate aus Acetyl- and Isopropyliden-D-Galactopyranosen," Journal f. prakt. Chemie. Band 1990, vol. 332, No. 1, pp. 28-36.
Vogel et al. "Synthesis of C-Glycosidic Galacturopates Suitable as Glycosyl Acceptors," Polish J. Chem. 2005, vol. 79, pp. 251-265.
Von Ahsen et al. "A Miniaturized High-Throughput Screening Assay for Fucosyltransferase VII," Analytical Biochemistry 2008, vol. 372, pp. 96-105.
Wang et al. "Efficient Glycoengineering of GM3 on Melanoma Cell and Monoclonal Antibody-Mediated Selective Killing of the Glycoengineered Cancer Cell," Bioorganic & Medicinal Chemistry 2007, vol. 15, pp. 7561-7567.
Watt et al. "Site-Specific Glycosylation of an Aglycosylated Human IgG1-Fc Antibody Protein Generates Neoglycoproteins with Enhanced Function," Chemistry & Biology 2003, vol. 10, 807-814.
Wilkinson et al. "Click Chemistry in Carbohydrate Based Drug Development and Glycobiology," In: Drug Design Research Perspectives, Editor: Stanley P. Kaplan, Nova Science Publishers, Inc. 2007, pp. 57-102.

Winterbourne et al. "2-Deoxy-2-Fluoro-L-Fucose and Its Effect on L-[1-$^{14}$C] Fucose Utilization in Mammalian Cells," Biochemical and Biophysical Research Communications 1979, vol. 87, pp. 989-992.
Wright et al. "Effect of Altered CH2-associated Carbohydrate Structure on the Functional Properties and In Vivo Fate of Chimeric Mouse-Human Immunoglobulin G1," J. Exp. Med 1994, vol. 180, pp. 1087-1096.
Wright et al. "In Vivo Trafficking and Catabolism of IgG1 Antibodies with Fc Associated Carbohydrates of Differing Structure," Glycobiology 2000, vol. 10, No. 12, pp. 1347-1355.
Wrodnigg et al. "Natural and Synthetic Iminosugars as Carbohydrate Processing Enzyme Inhibitors for Cancer Therapy," Anti-Cancer Agents in Medicinal Chemistry 2008, vol. 8, pp. 77-85.
Yamaguchi et al. "Glycoform-Dependent Conformational Alteration of the Fc Region of Human Immunoglobulin G1 as Revealed by NMR Spectroscopy," Biochimica et Biophysica Acta 2006, vol. 1760, pp. 693-700.
Yurchenco et al. "Fucosyl-Glycoprotein and Precursor Pools in HeLa Cells," Biochemistry 1975, vol. 14, No. 14, 3107-3114.
Yurchencol et al. "Equilibration of Fucosyl Glycoprotein Pools in HeLa Cells," Biochemistry 1977, vol. 16, No. 5, pp. 944-953.
Zeng et al. "High-Efficiency Labeling of Sialylated Glycoproteins on Living Cells," Nature Methods, pp. 1S-13S.
Zeng et al. "High-Efficiency Labeling of Sialylated Glycoproteins on Living Cells," Nature Methods 2009, vol. 6, No. 3, pp. 207-209.
Zhao et al. "Deletion of Core Fucosylation on α3β1 Integrin Down-Regulates Its Functions," The Journal of Biological Chemistry 2006, vol. 281, No. 50, pp. 38343-38350.
Zhou et al. "Development of a Simple and Rapid Method for Producing Non-Fucosylated Oligomannose Containing Antibodies With Increased Effector Function," Biotechnology and Bioengineering 2008, vol. 99, No. 3, pp. 652-665.
Zeitler et al., "Inhibition of L-Fucokinase From Rat Liver by L-Fucose Analogues In Vitro, J. Enzyme Inhibition," 11(4):265-273, 1997.
Shield et al., "Enzymic formation of potential anticancer and antiviral inosine analogs," Experientia, Birkhaeuser Verlag. Basel, 52(9):878-881, 1996.
Yuan et al., "Cell Surface Associated Alpha-1-Fucose Moieties Modulate Human Breast Cancer Neoplastic Progression," Pathology & Oncology Research, 14(2):145-156, 2008.
Haltiwanger et al., "Fucose is on the Trail of Colon Cancer," Gastroenterology 137(1):36-39, 2009.
Opposition filed in EP Patent No. 2282773, which corresponds to U.S. Pat. No. 8,163,551.
Opposition filed in JP Patent No. 5624535, which corresponds to U.S. Pat. No. 8,163,551.
Goodarzi et al., "Decreased branching, increased focusylation and changed sialylation of alpha-1-proteinase inhibitor in breast and ovarian cancer," Clinica Chimica Acts 236:161-171, 1995.
Imahori et al., "2-Deoxy-2-(18F)Fluoro-L-Fucose, a Potential Agent for Regional Fucose Utilization Studies Associated with Glycoprotein Synthesis," CYRIC Annual Report, 1984.

* cited by examiner

B

C

D

E

F

A

METHODS OF INHIBITION OF PROTEIN FUCOSYLATION IN VIVO USING FUCOSE ANALOGS

CROSS-REFERENCES TO RELATED APPLICATIONS

This application is a continuation of U.S. application Ser. No. 13/814,083 filed on Feb. 4, 2013, which is the national stage filing under 35 U.S.C. § 371 of International Application No. PCT/US2011/046857 filed Aug. 5, 2011, which claims the benefit of U.S. Provisional Application No. 61/371,116, filed Aug. 5, 2010, the disclosures of each are incorporated by reference herein in their entirety.

BACKGROUND OF THE INVENTION

L-fucose, also referred to as 6-deoxy-L-galactose, is a monosaccharide that is a component of some N- and O-linked glycans and glycolipids in animals. (See Becker and Lowe, Glycobiology 13:41R-51R (2003).) Fucose is typically added as a terminal modification to glycans, including glycans attached to blood group antigens, selectins and antibodies. Fucose can be attached to glycans via α(1,2)-, α(1,3)-, α(1,4)- and α(1,6)-linkages by specific fucosyltransferases. α(1,2)-fucose linkages are typically associated with the H-blood group antigens. α(1,3)- and α(1,4)-fucose linkages are associated with modification of Lewis$^x$ antigens. α(1,6)-fucose linkages are associated with N-linked GlcNAc molecules, such as those on antibodies.

Fucosylation of proteins is believed to play a role in mammalian development. Mice homozygous for a targeted mutation of the FX gene exhibit pleiotropic abnormalities including a lethal phenotype. Reduced recovery of mice from heterozygous crosses was also reported. (Becker et al., Mammalian Genome 14:130-139 (2003). Aberrant protein fucosylation has been proposed to be associated with human disease, including up-regulation of sialyl Lewis$^x$ and sialyl Lewis$^y$ in cancers. These glycans are ligands for E- and P-selectin molecules. In it speculated that increases in sialyl Lewis$^x$ and sialyl Lewis$^y$ glycans on cancer cells increases metastases through interaction with E- and P-selectins on endothelium. Increased fucosylated glycans have also been observed in patients with rheumatoid arthritis. Currently, however, there are no approved therapeutic approaches targeting protein fucosylation levels.

SUMMARY OF THE INVENTION

The methods and compositions described herein are premised in part on the unexpected results presented in the Examples, showing that animals administered a fucose analog have reduced protein fucosylation. Fucosylation of antibodies and other proteins can be modulated using the fucose analogs described herein.

In one aspect, methods and compositions for the in vivo production of defucosylated proteins are provided. Animals, such as mammals, administered a fucose analog (having formula I, II, III, IV, V or VI) produce proteins, such as cell surface proteins, having reduced fucosylation. The reduction in fucosylation is relative to animals untreated with the fucose analogs having formula I, II, III, IV, V or VI, respectively.

In a related aspect, methods and compositions for the in vivo production of antibodies and antibody derivatives with reduced core fucosylation are provided. Animals administered a fucose analog (having formula I, II, III, IV, V or VI) produce antibodies and antibody derivatives having reduced core fucosylation (i.e., reduced fucosylation of N-acetylglucosamine of the complex N-glycoside-linked sugar chains bound to the Fc region through the N-acetylglucosamine of the reducing terminal of the sugar chains). The reduction in core fucosylation is relative to animals untreated with the fucose analogs of having formula I, II, III, IV, V or VI, respectively.

In another aspect, pharmaceutical compositions containing fucose analogs and formulated for administration to a target animal are provided. The fucose analogs can be formulated for administration to an animal to inhibit or reduce fucosylation in vivo.

These and other aspects of the present invention may be more fully understood by reference to the following detailed description, non-limiting examples of specific embodiments, and the appended figures.

DETAILED DESCRIPTION OF THE INVENTION

Definitions

Figure 1:
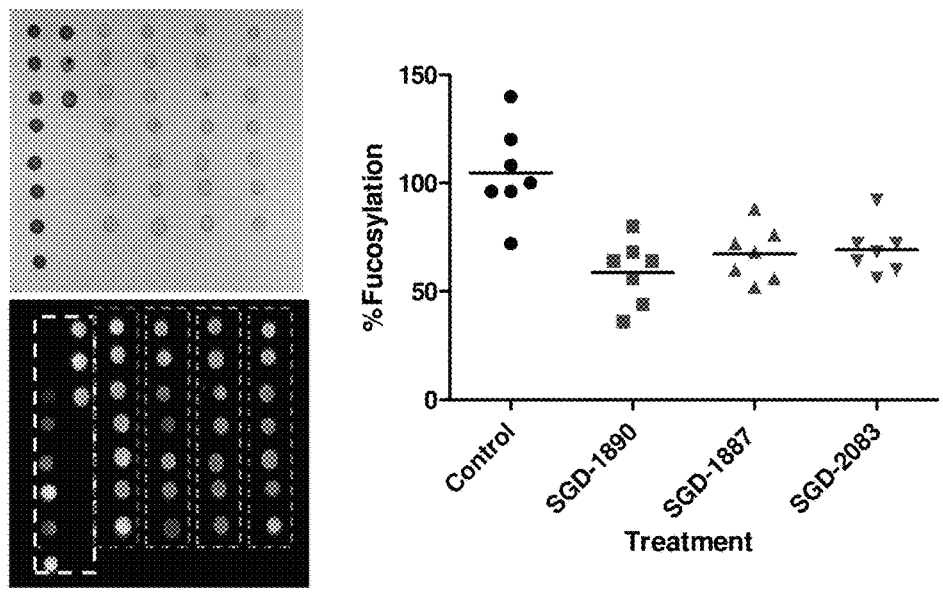
FIG. 1 shows the results of administration of fucose analogs (via ip injection) on antibody fucosylation. Dot blots are shown on the left panel and a graph is shown on the right panel. The dot blot protein loading levels (upper left) and fucose-specific bioluminescence (lower left) for antibody cAC10 standards (lower dot blot, left most dashed rectangle and corresponding columns of upper dot blot), untreated control (lower dot blot, second dashed rectangle from the left and corresponding column of upper dot blot), and alkynyl fucose (SGD-1887; lower dot blot, middle dashed rectangle and corresponding column of upper dot blot), alkynyl fucose peracetate (SGD-1890; lower dot blot, second dashed rectangle from the right and corresponding column of upper dot blot), and 2-fluorofucose (SGD-2083; lower dot blot, right most rectangle and corresponding column of upper dot blot). After correcting for loading level, the % fucosylation is shown on the graph at the right.

The term "antibody" refers to (a) immunoglobulin polypeptides and immunologically active portions of immunoglobulin polypeptides, i.e., polypeptides of the immunoglobulin family, or fragments thereof, that contain an antigen binding site(s) that immunospecifically binds to a specific antigen and have an Fc domain comprising a complex N-glycoside-linked sugar chain(s), or (b) conservatively substituted derivatives of such immunoglobulin polypeptides or fragments that immunospecific ally bind to the antigen. Antibodies are generally described in, for example, Harlow & Lane, Antibodies: *A Laboratory Manual* (Cold Spring Harbor Laboratory Press, 1988).

An "antibody derivative" means an antibody, as defined above (including an antibody fragment), or Fc domain or region of an antibody comprising a complex N-glycoside linked sugar chain, that is modified by covalent attachment of a heterologous molecule such as, e.g., by attachment of a heterologous polypeptide (e.g., a ligand binding domain of heterologous protein), or by glycosylation (other than core fucosylation), deglycosylation (other than non-core fucosylation), acetylation, phosphorylation or other modification not normally associated with the antibody or Fc domain or region.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

The term "Fc region" refers to the constant region of an antibody, e.g., a $C_H1$-hinge-$C_H2$-$C_H3$ domain, optionally having a $C_H4$ domain, or a conservatively substituted derivative of such an Fc region.

The term "Fc domain" refers to the constant region domain of an antibody, e.g., a $C_H1$ hinge, $C_H2$, $C_H3$ or $C_H4$ domain, or a conservatively substituted derivative of such an Fc domain.

An "antigen" is a molecule to which an antibody or antibody derivative specifically binds.

The terms "specific binding" and "specifically binds" mean that the antibody or antibody derivative will bind, in a highly selective manner, with its corresponding target antigen and not with the multitude of other antigens. Typically, the antibody or antibody derivative binds with an affinity of at least about $1 \times 10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The terms "inhibit" or "inhibition of" means to reduce by a measurable amount, or to prevent entirely.

As used herein, "alkynyl fucose peracetate" refers to any or all forms of alkynyl fucose (5-ethynylarabinose) with acetate groups on positions $R^{1-4}$ (see formula I and II, infra), including 6-ethynyl-tetrahydro-2H-pyran-2,3,4,5-tetrayl tetraacetate, including the (2S,3S,4R,5R,6S) and (2R,3S,4R,5R,6S) isomers, and 5-((S)-1-hydroxyprop-2-ynyl)-tetrahydrofuran-2,3,4-triyl tetraacetate, including the (2S,3S,4R,5R) and (2R,3S,4R,5R) isomers, and the aldose form, unless otherwise indicated by context. The terms "alkynyl fucose triacetate", "alkynyl fucose diacetate" and "alkynyl fucose monoacetate" refer to the indicated tri-, di- and mono-acetate forms of alkynyl fucose, respectively.

Unless otherwise indicated by context, the term "alkyl" refers to an unsubstituted saturated straight or branched hydrocarbon having from 1 to 20 carbon atoms (and all combinations and subcombinations of ranges and specific numbers of carbon atoms therein), unless otherwise specified. An alkyl group of 1 to 3, 1 to 8 or 1 to 10 carbon atoms is preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2- pentyl, 3-methyl-3-pentyl, 2-methyl-3-pentyl, 2,3-dimethyl-2-butyl, and 3,3-dimethyl-2-butyl.

Alkyl groups, whether alone or as part of another group, when substituted can be substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and CN; where each R' is independently selected from —H, —$C_1$-$C_8$ alkyl, —$C_2$-$C_8$ alkenyl, —$C_2$-$C_8$ alkynyl, or aryl.

Unless otherwise indicated by context, the terms "alkenyl" and "alkynyl" refer to unsubstituted or optionally substituted (were indicated) straight and branched carbon chains having from 2 to 20 carbon atoms (and all combinations and subcombinations of ranges and specific numbers of carbon atoms therein), with from 2 to 3, 2 to 4, 2 to 8 or 2 to 10 carbon atoms being preferred. An alkenyl chain has at least one double bond in the chain and an alkynyl chain has at least one triple bond in the chain. Examples of alkenyl groups include, but are not limited to, ethylene or vinyl, allyl, -1 butenyl, -2 butenyl, -isobutylenyl, -1 pentenyl, -2 pentenyl, 3-methyl-1-butenyl, -2 methyl 2 butenyl, and -2,3 dimethyl 2 butenyl. Examples of alkynyl groups include, but are not limited to, acetylenic, propargyl, acetylenyl, propynyl, -1 butynyl, -2 butynyl, -1 pentynyl, -2 pentynyl, and -3 methyl 1 butynyl.

Alkenyl and alkynyl groups, whether alone or as part of another group, when substituted can be substituted with one or more groups, preferably 1 to 3 groups (and any additional substituents selected from halogen), including but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —$C_1$-$C_8$ alkyl, —$C_2$—C alkenyl, —$C_2$-$C_8$ alkynyl, or aryl.

Unless otherwise indicated by context, the term "alkylene" refers to an unsubstituted saturated branched or straight chain hydrocarbon radical having from 1 to 20 carbon atoms (and all combinations and subcombinations of ranges and specific numbers of carbon atoms therein), with from 1 to 8 or 1 to 10 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like.

Alkylene groups, whether alone or as part of another group, when substituted can be substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or aryl.

"Alkenylene" refers to an unsaturated, branched or straight chain or cyclic hydrocarbon radical of an alkenyl group (as described above), and having two monovalent radical centers derived by the removal of two hydrogen atoms from the same or two different carbon atoms of a parent alkene. An "alkenylene" group can be unsubstituted or optionally substituted (were indicated), as described above for alkenyl groups. In some embodiments, an "alkenylene" group is not substituted.

"Alkynylene" refers to an unsaturated, branched or straight chain or cyclic hydrocarbon radical of an alkynyl group (as described above), and having two monovalent radical centers derived by the removal of two hydrogen atoms from the same or two different carbon atoms of a parent alkyne. An "alkynylene" group can be unsubstituted or optionally substituted (were indicated), as described above for alkynyl groups. In some embodiments, an "alkynylene" group is not substituted.

Unless otherwise indicated by context, the term "aryl" refers to a substituted or unsubstituted monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to: halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —NH2, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or aryl.

Unless otherwise indicated by context, the term "heterocycle" refers to a substituted or unsubstituted monocyclic ring system having from 3 to 7, or 3 to 10, ring atoms (also referred to as ring members) wherein at least one ring atom is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960). Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, fucosyl, azirdinyl, azetidinyl, oxiranyl, oxetanyl, and tetrahydrofuranyl.

A heterocycle group, whether alone or as part of another group, when substituted can be substituted with one or more groups, preferably 1 to 2 groups, including but not limited to: —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or -aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; or position 2, 3, or 4 of an azetidine. Exemplary carbon bonded heterocycles can include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; and position 4 of a morpholine. Still more typically, nitrogen bonded heterocycles include 1-aziridyl, 1-azetidyl, 1-pyrrolyl, 1-imidazolyl, 1-pyrazolyl, and 1-piperidinyl.

Unless otherwise noted, the term "carbocycle," refers to a substituted or unsubstituted, saturated or unsaturated non-aromatic monocyclic ring system having from 3 to 6 ring atoms (and all combinations and subcombinations of ranges and specific numbers of carbon atoms therein) wherein all of the ring atoms are carbon atoms.

Carbocycle groups, whether alone or as part of another group, when substituted can be substituted with, for example, one or more groups, preferably 1 or 2 groups (and any additional substituents selected from halogen), including, but not limited to: halogen, C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or aryl.

Examples of monocyclic carbocylic substituents include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, cyclooctyl, -1,3-cyclohexadienyl, -1,4-cyclohexadienyl, -1,3-cycloheptadienyl, -1,3,5-cycloheptatrienyl, and -cyclooctadienyl.

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—(C$_1$-C$_{10}$ alkylene)aryl" or "—C$_1$-C$_{10}$ alkylene(aryl)" refers to a C$_1$-C$_{10}$ alkylene radical as defined herein wherein the alkylene radical is attached to the pendant molecule at any of the carbon atoms of the alkylene radical and one of the hydrogen atom bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are active and chemically stable and that can be readily synthesized by techniques known in the art as well as those methods set forth herein.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which the fucose analog is administered.

"Small electron-withdrawing groups" refers to any substituent that has greater electronegativity at the site of substituent attachment than, e.g., a hydrogen atom or hydroxy group or relative to the substituent present in fucose at that site. Generally, the small electron-withdrawing group has 10 or fewer atoms (other than hydrogen) and includes groups such as nitro; cyano and cyanoalkyl (e.g., —CH$_2$CH$_2$CN); halogens; acetylene or other alkynes or halo alkynes (e.g., —C≡CCF$_3$); alkenes or halo alkenes; allenes; carboxylic acids, ester, amides and halo substituted forms thereof; sulfonic and phosphonic acids, esters and amides, and halo substituted forms thereof; haloalkyl groups (e.g., —CF$_3$, —CHF$_2$, —CH$_2$CF$_3$), acyl and haloacyl groups (e.g., —C(O)CH$_3$ and —C(O)CF$_3$); alkylsulfonyl and haloalkylsulfonyl (e.g., —S(O)$_2$alkyl and —S(O)$_2$haloalkyl); aryloxy (e.g., phenoxy and substituted phenoxy); aralkyloxy (e.g, benzyloxy and substituted benzyloxy); and oxiranes. Preferred small electron-withdrawing groups are those having 8, 7 or 6 or fewer atoms (other than hydrogen).

The fucose analogs are typically substantially pure from undesired contaminant. This means that the analog is typically at least about 50% w/w (weight/weight) purity, as well as being substantially free from interfering proteins and other contaminants. Sometimes the agents are at least about 80% w/w and, more preferably at least 90% or about 95% w/w purity. Using conventional purification techniques, homogeneous product of at least 99% w/w can be obtained.

General

The invention provides methods and compositions for reducing protein fucosylation in an animal. The methods are premised in part on the unexpected results presented in the Examples showing that administering a fucose analog to a subject (e.g., a mammal) results in an antibody or antibody derivative having reduced core fucosylation, and other proteins also having reduced fucosylation. "Reduced fucosylation" in the context of proteins generally refers to reduced addition of fucose to glycans via α(1,2)-, α(1,3)-, α(1,4)- and α(1,6)-linkages. "Core fucosylation" in the context of an antibody refers to addition of fucose ("fucosylation") to N-acetylglucosamine ("GlcNAc") at the reducing terminal of an N-linked glycan of an antibody. "Reduced core fucosylation" in the context of an antibody refers to a reduction of fucose linked to N-acetylglucosamine ("GlcNAc") at the reducing terminal of an N-linked glycan of an antibody, as compared to an untreated animal.

In the various aspects described herein, the animal to which the fucose analog is administered is typically a mammal and is preferably human. The invention therefore further provides methods and compositions for reducing protein fucosylation in a mammal, such as a human.

In other aspects, pharmaceutical compositions of fucose analogs and pharmaceutical excipients are provided in which an effective amount of a fucose analog(s) is in admixture with the excipients, suitable for administration to a animal. In some embodiments, the fucose analog is in dry form (e.g., lyophilized), optionally with stabilizers that enhance the composition stability for longer term storage. In some embodiments, a pharmaceutical composition of a fucose analogs and pharmaceutical excipients is formulated for administration to a mammal. In some further embodiments, a pharmaceutical composition of a fucose analogs and pharmaceutical excipients is formulated for administration to a human.

In some embodiments, fucosylation of complex N-glycoside-linked sugar chains bound to the Fc region (or domain) of an antibody is reduced. As used herein, a "complex N-glycoside-linked sugar chain" is typically bound to asparagine 297 (according to the numbering system of Kabat), although a complex N-glycoside linked sugar chain can also be linked to other asparagine residues. As used herein, the complex N-glycoside-linked sugar chain has a bianntennary composite sugar chain, mainly having the following structure:

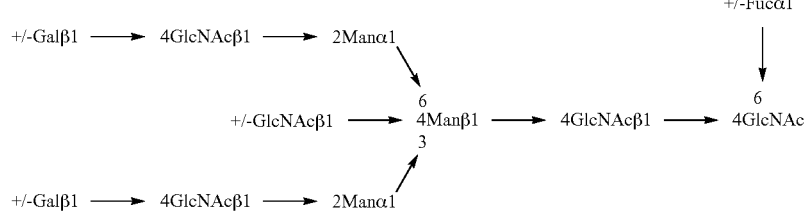

where ± indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like, but excludes chains with a high mannose component.

According to the present methods, typically only a minor amount of fucose is incorporated into the sugar chain(s) (e.g., a glycan or complex N-glycoside-linked sugar chains) after administering a fucose analog. For example, in various embodiments, less than about 60%, less than about 50%, less than about 40%, less than about 30%, less than about 20%, less than about 15%, less than about 10%, less than about 5%, or less than about 1% of the antibodies in the serum of the animal (e.g., a mammal, such as a human) are core fucosylated, as compared to an animal not receiving the fucose analog. In some embodiments, substantially none (i.e., less than 0.5%) of the antibodies in the serum of the animal are not core fucosylated, as compared to an animal not receiving the fucose analog.

In some embodiments, protein fucosylation is reduced by about 60%, by about 50%, by about 40%, by about 30%, by about 20%, by about 15%, by about 10%, by about 5%, or by about 1% for cell surface proteins in the animal (e.g., a mammal, such as a human) are fucosylated, as compared to an animal not receiving the fucose analog. In some embodiments, protein fucosylation via α(1,2)-linkage is reduced by about 60%, by about 50%, by about 40%, by about 30%, by about 20%, by about 15%, by about 10%, by about 5%, or by about 1% for cell surface proteins in the animal (e.g., a mammal, such as a human) are fucosylated, as compared to an animal not receiving the fucose analog.

In some embodiments, protein fucosylation via α(1,3)-linkage is reduced by about 60%, by about 50%, by about 40%, by about 30%, by about 20%, by about 15%, by about 10%, by about 5%, or by about 1% for cell surface proteins in the animal (e.g., a mammal, such as a human) are fucosylated, as compared to an animal not receiving the fucose analog. In some embodiments, protein fucosylation via α(1,4)-linkage is reduced by about 60%, by about 50%, by about 40%, by about 30%, by about 20%, by about 15%, by about 10%, by about 5%, or by about 1% for cell surface proteins in the animal (e.g., a mammal, such as a human) are fucosylated, as compared to an animal not receiving the fucose analog.

In some embodiments, protein fucosylation via α(1,6)-linkage is reduced by about 60%, by about 50%, by about 40%, by about 30%, by about 20%, by about 15%, by about 10%, by about 5%, or by about 1% for cell surface proteins in the animal (e.g., a mammal, such as a human) are fucosylated, as compared to an animal not receiving the fucose analog.

In some embodiments, fucosylation of white blood cells in the serum of the animal (e.g., a mammal, such as a human) is reduced by at least about 60%, at least about 50%, at least about 40%, at least about 30%, at least about 20%, at least about 15%, at least about 10%, or at least about 5%, as compared to an animal not receiving the fucose analog. In some embodiments, fucosylation via α(1,3) linkages of white blood cells in the serum of the animal (e.g., a mammal, such as a human) is reduced by at least about 60%, at least about 50%, at least about 40%, at least about 30%, at least about 20%, at least about 15%, at least about 10%, or at least about 5%, as compared to an animal not receiving the fucose analog. In some embodiments, fucosylation via α(1,4) linkages of white blood cells in the serum of the animal (e.g., a mammal, such as a human) is reduced by at least about 60%, at least about 50%, at least about 40%, at least about 30%, at least about 20%, at least about 15%, at least about 10%, or at least about 5%, as compared to an animal not receiving the fucose analog.

In some embodiments, fucosylation of antibodies in the serum of the animal (e.g., a mammal, such as a human) is reduced by at least about 60%, at least about 50%, at least about 40%, at least about 30%, at least about 20%, at least about 15%, at least about 10%, or at least about 5%, as compared to an animal not receiving the fucose analog.

In certain embodiments, only a minor amount of a fucose analog (or a metabolite or product of the fucose analog) is incorporated into glycans (e.g., the complex N-glycoside-linked sugar chain(s)) of the antibody, antibody derivative or other glycans of proteins. For example, in various embodiments, less than about 60%, less than about 40%, less than about 30%, less than about 20%, less than about 15%, less than about 10%, less than about 5%, or less than about 1% of the fucose analog (or a metabolite or product of the fucose analog) is incorporated into glycans of the antibodies in the serum of the animal, as compared to an animal not receiving the fucose analog. In some embodiments, less than about 60%, less than about 40%, less than about 30%, less than about 20%, less than about 15%, less than about 10%, less than about 5%, or less than about 1% of the fucose analog (or a metabolite or product of the fucose analog) is incorporated into glycans of cell surface proteins of the animal, as compared to an animal not receiving the fucose analog.

In some embodiments, less than about 60%, less than about 40%, less than about 30%, less than about 20%, less than about 15%, less than about 10%, less than about 5%, or less than about 1% of the fucose analog (or a metabolite or product of the fucose analog) is incorporated into glycans of white blood cells in the serum of the animal, as compared to an animal not receiving the fucose analog.

Fucose Analogs

Suitable fucose analogs for the methods of the present invention (identified below as Formula I, II, III, IV, V and VI) are those that can be safely administered to a mammal in an amount effective to inhibit core fucosylation of complex N-glycoside-linked sugar chains of antibodies or antibody derivatives. Fucose analogs are described in Published US Patent Application 2009-0317869 that reduce the incorporation of fucose into complex N-glycoside-linked sugar chains of antibodies or antibody derivatives produced by host cells in vitro. The fucose analog can be given to a subject animal (e.g., a mammal) by parental, orally or other suitable mode of administration.

In some embodiments, a fucose analog (or an intracellular metabolite or product of the fucose analog) inhibits an enzyme(s) in the fucose salvage pathway. (As used herein, an intracellular metabolite can be, for example, a GDP-modified analog or a fully or partially de-esterified analog. A product can be, for example, a fully or partially de-esterified analog.) For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (such as a 1,2-fucosyltransferase, 1,3-fucosyltransferase, 1,4-fucosyltransferase, or 1,6-fucosyltransferase (e.g., the FUT8 protein)). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In some embodiments, the fucose analog has the following formula (I) or (II):

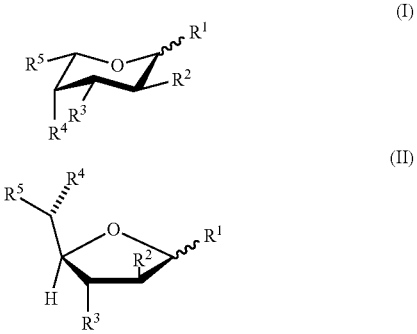

or a biologically acceptable salt or solvate of the analog, wherein each of formula (I) or (II) can be the alpha or beta anomer or the corresponding aldose form. In the above formulae, each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OC(O)$CH_2O$($CH_2CH_2O$)$_n$$CH_3$, —OC(O)$CH_2CH_2O$($CH_2CH_2O$)$_n$$CH_3$, —O-tri-$C_1$-$C_3$ alkyl silyl, —O$C_1$-$C_{10}$ alkyl, —O$CH_2$OC(O) alkyl, —O$CH_2$OC(O) alkenyl, —O$CH_2$OC(O) alkynyl, —O$CH_2$OC(O) aryl, —O$CH_2$OC(O) heterocycle, —O$CH_2$OC(O)O alkyl, —O$CH_2$OC(O)O alkenyl, —O$CH_2$OC(O)O alkynyl, —O$CH_2$OC(O)O aryl and —O$CH_2$OC(O)O heterocycle, wherein each n is an integer independently selected from 0-5; and $R^5$ is selected from the group consisting of —C≡CH, —C≡C$CH_3$, —$CH_2$C≡CH, —C(O)O$CH_3$, —CH(OAc)$CH_3$, —CN, —$CH_2$CN, —$CH_2$X (wherein X is F, Br, Cl or I), —$CHX_2$ (wherein each X is F, Br or Cl) and methoxiran.

In some embodiments, the fucose analog has formula (I) or (II), wherein: each of $R^1$-$R^4$ is independently selected from the group consisting of —OH, —OC(O)H, —OC(O)$C_1$-$C_{10}$ alkyl, —OC(O)aryl, —OC(O)heterocycle, —OC(O)$C_1$-$C_{10}$ alkylene(aryl), —OC(O)$C_1$-$C_{10}$ alkylene(heterocycle), —OC(O)$CH_2CH_2O(CH_2CH_2O)_nCH_3$, —OC(O)$CH_2CH_2O(CH_2CH_2O)_nCH_3$, —O-tri-$C_1$-$C_3$ silyl, —O$C_1$-$C_{10}$ alkyl, —O$CH_2OC(O)$ alkyl, —O$CH_2OC(O)O$ alkyl, —O$CH_2OC(O)$ aryl, and —O$CH_2OC(O)O$ aryl, wherein each n is an integer independently selected from 0-5; and $R^5$ is selected from the group consisting of —C≡CH, —C≡C$CH_3$, —$CH_2$C≡CH, —C(O)O$CH_3$, —CH(OAc)$CH_3$, —CN, —$CH_2$CN, —$CH_2$X (wherein X is F, Br, Cl or I), —$CHX_2$ (wherein each X is F, Br or Cl), and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡C$CH_3$, —$CH_2$C≡CH, —C(O)O$CH_3$, —CH(OAc)$CH_3$, —CN, —$CH_2$CN, —$CH_2$X (wherein X is F, Br, Cl or I), —$CHX_2$ (wherein each X is F, Br or Cl), and methoxiran.

In some embodiments, the fucose analog has formula (I) or (II), wherein each of $R^1$-$R^4$ is independently selected from the group consisting of —O-tri-$C_1$-$C_3$ silyl and —O$C_1$-$C_{10}$ alkyl; and $R^5$ is selected from the group consisting of —C≡CH, —C≡C$CH_3$, —$CH_2$C≡CH, —C(O)O$CH_3$, —CH(OAc)$CH_3$, —CN, —$CH_2$CN, —$CH_2$X (wherein X is Br, Cl or I), and methoxiran.

In some embodiments, the fucose analog has formula (I) or (II), wherein each of $R^1$-$R^4$ is independently selected from the group consisting of —O$CH_2OC(O)$ alkyl, —O$CH_2OC(O)$ alkenyl, —O$CH_2OC(O)$ alkynyl, —O$CH_2OC(O)$ aryl, —O$CH_2OC(O)$ heterocycle, —O$CH_2OC(O)O$ alkyl, —O$CH_2OC(O)O$ alkenyl, —O$CH_2OC(O)O$ alkynyl, —O$CH_2OC(O)O$ aryl, and —O$CH_2OC(O)O$ heterocycle; and $R^5$ is selected from the group consisting of —C≡CH, —C≡C$CH_3$, —$CH_2$C≡CH, —C(O)O$CH_3$, —CH(OAc)$CH_3$, —CN, —$CH_2$CN, —$CH_2$X (wherein X is F, Br, Cl or I), —$CHX_2$ (wherein each X is F, Br or Cl), and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡C$CH_3$, —$CH_2$C≡CH, —C(O)O$CH_3$, —CH(OAc)$CH_3$, —CN, —$CH_2$CN, and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —$CH_2$F, —$CH_2$Br, and —$CH_2$Cl.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —$CHF_2$, —$CHBr_2$, and —$CHCl_2$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡C$CH_3$ and —$CH_2$C≡CH.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡C$CH_3$, —$(CH_2)_n$(CN) (where n=0 or 1) and —CO(O)$CH_3$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡C$CH_3$, —$CH_2$CN and —CO(O)$CH_3$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡C$CH_3$, —CH(OAc)$CH_3$, —$CH_2$CN, and —CO(O)$CH_3$.

In some embodiments, the fucose analog has formula (I) or (II), wherein $R^5$ is as defined herein, and each of $R^1$-$R^4$ is hydroxyl or —OC(O)$C_1$-$C_{10}$ alkyl.

In some embodiments, the fucose analog has formula (I) or (II), wherein $R^5$ is as defined herein, and each of $R^1$-$R^4$ is hydroxyl or —OAc.

In some embodiments, the fucose analog has formula (I) or (II), wherein each of $R^1$-$R^4$ is independently selected from the group consisting of —OH, and OC(O)$C_1$-$C_{10}$ alkyl; and $R^5$ is selected from the group consisting of —C≡CH, —C≡C$CH_3$, —CH(OAc)$CH_3$, —$CH_2$CN, —CO(O)$CH_3$, —$CH_2$F and —$CHF_2$ In some embodiments, the fucose analog has formula (I) or (II), wherein each of $R^1$-$R^4$ is independently selected from the group consisting of —OH, and —OAc; and $R^5$ is selected from the group consisting of —C≡CH, —C≡CCH$_3$, —CH(OAc)CH$_3$, —CH$_2$CN, —CO(O)CH$_3$, —CH$_2$F and —CHF$_2$ In some embodiments, the fucose analog has formula (I) or (II), wherein each of $R^1$-$R^4$ is independently selected from the group consisting of —OH, and —OC(O)C$_1$-C$_{10}$ alkyl; and $R^5$ is selected from the group consisting of —C≡CH, —CH$_2$F and —CHF$_2$.

In some embodiments, the fucose analog has formula (I) or (II), wherein each of $R^1$-$R^4$ is independently selected from the group consisting of —OH, and —OAc; and $R^5$ is selected from the group consisting of —C≡CH, —CH$_2$F and —CHF$_2$.

In some embodiments, the fucose analog has formula (I) or (II), wherein each of $R^1$-$R^4$ is independently selected from the group consisting of —OH, and —OC(O)C$_1$-C$_{10}$ alkyl; and $R^5$ is —C≡CH.

In some embodiments, the fucose analog has formula (I) or (II), wherein each of $R^1$-$R^4$ is independently selected from the group consisting of —OH, and —OAc; and $R^5$ is —C≡CH.

In some embodiments, the fucose analog has formula (I) or (II), wherein each of $R^1$-$R^4$ is independently selected from the group consisting of —OH, and —OC(O)C$_1$-C$_{10}$ alkyl; and $R^5$ is —CHF$_2$.

In some embodiments, the fucose analog has formula (I) or (II), wherein each of $R^1$-$R^4$ is independently selected from the group consisting of —OH, and —OAc; and $R^5$ is —CHF$_2$.

In some embodiments, the fucose analog has formula (I) or (II), wherein each of $R^1$-$R^4$ is —OH or an ester selected from the group consisting of —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), —OC(O)C$_2$-C$_{10}$ alkynylene(heterocycle), —OC(O)CH$_2$O(CH$_2$CH$_2$O)$_n$CH$_3$ (where n is 0-5), and —OC(O)CH$_2$CH$_2$O(CH$_2$CH$_2$O)$_n$CH$_3$ (where n is 0-5); and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is F, Br, Cl or I), —CHX$_2$ (wherein each X is F, Br or Cl), and methoxiran.

In some embodiments, the fucose analog has formula (I) or (II), wherein each of $R^1$-$R^4$ is independently selected from the group consisting of —OH, and —OC(O)C$_1$-C$_{10}$ alkyl; and $R^5$ is —CH$_2$X (wherein X is F, Br, Cl or I).

In some embodiments, the fucose analog has formula (I) or (II), wherein each of $R^1$-$R^4$ is independently selected from the group consisting of —OH, and —OAc; and $R^5$ is —CH$_2$X (wherein X is F, Br, Cl or I).

In some embodiments, the fucose analog has formula (I) or (II), wherein each of $R^1$-$R^4$ is independently selected from the group consisting of —OH, and —OC(O)C$_1$-C$_{10}$ alkyl; and $R^5$ is —CH$_2$Br.

In some embodiments, the fucose analog has formula (I) or (II), wherein each of $R^1$-$R^4$ is independently selected from the group consisting of —OH, and —OAc; and $R^5$ is —CH$_2$Br.

In some embodiments, the fucose analog has a molecular weight of less than 2000 daltons. In some embodiments, the fucose analog has a molecular weight of less than 1000 daltons.

In some embodiments, $R^5$ is not substituted.
In some embodiments, each of $R^1$-$R^4$ is not substituted.
In some embodiments, $R^5$ is not a ketone (—C(O)alkyl).

In some embodiments, $R^5$ is not —CH(CH$_3$)OAc.
In some embodiments, $R^5$ is not —CH(CH$_3$)OAc, when each of $R^1$-$R^4$ is —OAc.
In some embodiments, $R^5$ is not —C≡CH.
In some embodiments, $R^5$ is not —C≡CH, when any of $R^1$-$R^4$ is —OAc.
In some embodiments, $R^5$ is not —C≡CH, when any of $R^1$-$R^4$ is —OC(O)alkyl.
In some embodiments, $R^5$ is not —C≡CH, when each of $R^1$-$R^4$ is —OC(O)alkyl.
In some embodiments, $R^5$ is not —C≡CH$_3$ when each of $R^1$-$R^4$ is OH.

In some embodiments, the fucose analog is alkynyl fucose peracetate. In some embodiments, the fucose analog is alkynyl fucose triacetate. In some embodiments, the fucose analog is alkynyl fucose diacetate. In some embodiments, the fucose analog is mixture of alkynyl fucose peracetate, alkynyl fucose triacetate and alkynyl fucose diacetate.

In some embodiments, the fucose analog is mixture of alkynyl fucose peracetate, alkynyl fucose triacetate, alkynyl fucose diacetate and alkynyl fucose monoacetate.

In any of the various embodiments, the fucose analog is not fucose. In some embodiments, the fucose analog is not alkynyl fucose peracetate. In some embodiments, the fucose analog is not galactose or L-galactose.

In another group of embodiments, the fucose analog has the following formula (III) or (IV):

(III)

(IV)

or a biologically acceptable salt or solvate thereof, wherein each of formula (III) or (IV) can be the alpha or beta anomer or the corresponding aldose form; and wherein, each of $R^1$-$R^4$ is independently selected from the group consisting of fluoro, chloro, —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkenylene(aryl), —OC(O)C$_2$-C$_{10}$ alkynyl(aryl), —OC(O)C$_1$-C$_{10}$ alkylene (heterocycle), —OC(O)C$_2$-C$_{10}$ alkenylene(heterocycle), —OC(O)C$_2$-C$_{10}$ alkynylene(heterocycle), —OCH$_2$OC(O) alkyl, —OCH$_2$OC(O)O alkyl —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-C$_1$-C$_3$ alkylsilyl and —OC$_1$-C$_{10}$ alkyl, wherein each n is an integer independently selected from 0-5; and each of $R^{2a}$ and $R^{3a}$ is independently selected from the group consisting of H, F and Cl;

$R^5$ is selected from the group consisting of —CH$_3$, —CHF$_2$, —CH=C=CH$_2$, —C≡CH, —C≡CCH$_3$, —CH$_2$C≡CH, —C(O)OCH$_3$, —CH(OAc)CH$_3$, —CN, —CH$_2$CN, —CH$_2$X (wherein X is F, Br, Cl or I), and methoxiran;

wherein when $R^5$ is other than —CH=C=CH$_2$, —CH$_2$F or —CHF$_2$, at least one of $R^1$, $R^2$, $R^3$, $R^{2a}$ and $R^{3a}$ is fluoro or chloro.

In some embodiments of formulae (III) or (IV), $R^1$ is F.
In some embodiments of formulae (III) or (IV), $R^2$ is F.
In some embodiments of formulae (III) or (IV), $R^3$ is F.
In some embodiments of formulae (III) or (IV), $R^1$ and $R^2$ are each F.
In some embodiments of formulae (III) or (IV), $R^2$ and $R^{2a}$ are each F.
In some embodiments of formulae (III) or (IV), $R^1$, $R^3$ and $R^4$ are each independently selected from —OH and —OC(O)$C_1$-$C_{10}$ alkyl; $R^2$ is F; and $R^5$ is —CH$_3$.
In some embodiments of formulae (III) or (IV), $R^1$, $R^3$ and $R^4$ are each independently selected from —OH and —OAc; $R^2$ is F; and $R^5$ is —CH$_3$.
In some embodiments of formulae (III) or (IV), $R^1$, $R^3$ and $R^4$ are each independently selected from —OH and —OC(O)$C_1$-$C_{10}$ alkyl; $R^2$ is F; $R^{2a}$ and $R^{3a}$ are each H; and $R^5$ is —CH$_3$.
In some embodiments of formulae (III) or (IV), $R^1$, $R^3$ and $R^4$ are each independently selected from —OH and —OAc; $R^2$ is F; $R^{2a}$ and $R^{3a}$ are each H; and $R^5$ is —CH$_3$.
In some embodiments of formulae (III) or (IV), $R^1$, $R^2$, $R^3$ and $R^4$ are each independently selected from —OH and —OC(O)$C_1$-$C_{10}$ alkyl; $R^{2a}$ and $R^{3a}$ are each H; and $R^5$ is —CHF$_2$.
In some embodiments of formulae (III) or (IV), $R^1$, $R^2$, $R^3$ and $R^4$ are each independently selected from —OH and —OAc; $R^{2a}$ and $R^{3a}$ are each H; and $R^5$ is —CHF$_2$.
In some embodiments of formulae (III) or (IV), $R^1$, $R^2$, $R^3$ and $R^4$ are each independently selected from —OH and —OC(O)$C_1$-$C_{10}$ alkyl; $R^{2a}$ and $R^{3a}$ are each H; and $R^5$ is —CH$_2$F.
In some embodiments of formulae (III) or (IV), $R^1$, $R^2$, $R^3$ and $R^4$ are each independently selected from —OH and —OAc; $R^{2a}$ and $R^{3a}$ are each H; and $R^5$ is —CH$_2$F.

In another group of embodiments, the fucose analog has the following formula (V) or (VI):

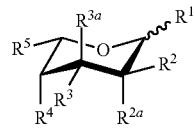

(V)

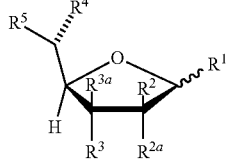

(VI)

or a biologically acceptable salt or solvate thereof, wherein each of formula (V) or (VI) can be the alpha or beta anomer or the corresponding aldose form; and wherein,
each of $R^1$, $R^2$, $R^{2a}$, $R^3$, $R^{3a}$ and $R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$ alkylsilyl, —O$C_1$-$C_{10}$ alkyl, and a small electron withdrawing group, wherein each n is an integer independently selected from 0-5;
$R^5$ is a member selected from the group consisting of —CH$_3$, —CHX$_2$, —CH$_2$X, —CH(X')—$C_1$-$C_4$ alkyl unsubstituted or substituted with halogen, —CH(X')—$C_2$-$C_4$ alkene unsubstituted or substituted with halogen, —CH(X')—$C_2$-$C_4$ alkyne unsubstituted or substituted with halogen, —CH=C($R^{10}$)($R^{11}$), —C(CH$_3$)=C($R^{12}$)($R^{13}$), —C($R^{14}$)=C=C($R^{15}$)($R^{16}$), —$C_3$ carbocycle unsubstituted or substituted with methyl or halogen, —CH(X')—$C_3$ carbocycle unsubstituted or substituted with methyl or halogen, $C_3$ heterocycle unsubstituted or substituted with methyl or halogen, —CH(X')—$C_3$ heterocycle unsubstituted or substituted with methyl or halogen, —CH$_2$N$_3$, —CH$_2$CH$_2$N$_3$, and benzyloxymethyl, or $R^5$ is a small electron withdrawing group; wherein $R^{10}$ is hydrogen or $C_1$-$C_3$ alkyl unsubstituted or substituted with halogen; $R^{11}$ is $C_1$-$C_3$ alkyl unsubstituted or substituted with halogen; $R^{12}$ is hydrogen, halogen or $C_1$-$C_3$ alkyl unsubstituted or substituted with halogen; $R^{13}$ is hydrogen, or $C_1$-$C_3$ alkyl unsubstituted or substituted with halogen; $R^{14}$ is hydrogen or methyl; $R^{15}$ and $R^{16}$ are independently selected from hydrogen, methyl and halogen; X is halogen; X' is halogen or hydrogen; and
additionally, each of $R^1$, $R^2$, $R^{2a}$, $R^3$ and $R^{3a}$ are optionally hydrogen; optionally two $R^1$, $R^2$, $R^{2a}$, $R^3$ and $R^{3a}$ on adjacent carbon atoms are combined to form a double bond between said adjacent carbon atoms; and
provided that at least one of $R^1$, $R^2$, $R^{2a}$, $R^3$, $R^{3a}$, $R^4$ and $R^5$ is a small electron withdrawing group, or $R^5$ comprises a halogen, site of unsaturation, carbocycle, heterocycle or azide, except when (i) $R^2$ and $R^{2a}$ are both hydrogen, (ii) $R^3$ and $R^{3a}$ are both hydrogen, (iii) $R^1$ is hydrogen, (iv) a double bond is present between said adjacent carbon atoms, or (v) $R^5$ is benzyloxymethyl; and
wherein protein, antibody or antibody derivative produced in vivo has reduced fucosylation compared to the protein, antibody or antibody derivative produced in vivo in the absence of the fucose analog.

In some embodiments of formulae (V) and (VI), $R^{2a}$ and $R^{3a}$ are each hydrogen.

In some embodiments of formulae (V) and (VI), $R^5$ is selected from the group consisting of —CH$_3$, —CH$_2$CH$_3$, —CH$_2$C≡CH, —CH=CHCH$_3$, -cyclopropyl, -oxirane, -oxirane substituted with methyl, —CH$_2$F, —CH$_2$Cl, —CH$_2$Br, —CH$_2$I, —CHF$_2$, —CH=C=CH$_2$, —CH$_2$N$_3$ and —CH$_2$CH$_2$N$_3$.

In some embodiments of formulae (V) and (VI), the small electron withdrawing group is selected from fluoro, chloro, bromo, —CHF$_2$, —CH=C=CH$_2$, —C≡CH, —C≡CCH$_3$, —CH$_2$C≡CH, —CO$_2$H, —C(O)OC$_1$-$C_4$ alkyl, —CH(OAc)CH$_3$, —CN, —CH$_2$CN, —CH$_2$X (wherein X is Br, Cl or I), and methoxiran.

In some embodiments of formulae (V) and (VI), $R^5$ is selected from the group consisting of —CH$_3$, —C≡CH, —CH$_2$F, —CH$_2$Br, and —CHF$_2$. In some further embodiments, each of $R^1$, $R^2$, $R^{2a}$, $R^3$, $R^{3a}$ and $R^4$ is independently selected from the group consisting of —OH, —OC(O)H, and —OC(O)$C_1$-$C_{10}$ alkyl.

In some embodiments of formulae (V) and (VI), the small electron withdrawing group is selected from fluoro, chloro, bromo, —CHF$_2$, —CH=C=CH$_2$, —C≡CH, —C≡CCH$_3$, —CH$_2$C≡CH, —CO$_2$H, —C(O)OC$_1$-C$_4$ alkyl, —CH(OAc) CH$_3$, —CN, —CH$_2$CN, —CH$_2$X (wherein X is Br, Cl or I), and methoxiran.

In some embodiments of formulae (V) and (VI), at least two of R$^1$, R$^2$, R$^{2a}$, R$^3$, R$^{3a}$ and R$^4$ are independently selected small electron withdrawing groups.

In some embodiments of formulae (V) and (VI), the fucose analog is selected from compounds of Tables 1, 2 or 3.

Pharmaceutical Compositions

Fucose analogs of formulae I, II, III, IV, V and VI (hereinafter 'fucose analogs') can be formulated for therapeutic applications. The fucose analogs can be formulated as pharmaceutical compositions comprising a therapeutically or prophylactically effective amount of the fucose analog and one or more pharmaceutically compatible (acceptable) ingredients. For example, a pharmaceutical or non-pharmaceutical composition typically includes one or more carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will typically contain a therapeutically effective amount of the fucose analog, typically in purified form, together with a suitable amount of carrier so as to provide the form for proper administration to the patient. The formulations correspond to the mode of administration.

The pharmaceutical compositions described herein can be in any form that allows for the composition to be administered to an animal (e.g., a mammal). The pharmaceutical compositions described herein can be in any form that allows for the composition to be administered to a mammal. The pharmaceutical compositions described herein can be in any form that allows for the composition to be administered to a human.

The compositions can be in the form of a solid or liquid. Typical routes of administration include, without limitation, oral, parenteral, sublingual, and ocular. Parenteral administration includes subcutaneous injections, intravenous, intramuscular, intrasternal injection or infusion techniques. Preferably, the compositions are administered parenterally or orally. These pharmaceutical compositions can be formulated so as to allow a fucose analog to be bioavailable upon administration of the composition to an animal. Compositions can also take the form of one or more dosage units, where for example, a tablet can be a single dosage unit, and a container of a fucose analog in solid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the fucose analog, the manner of administration, the composition employed, and the severity of the disease or condition being treated.

The pharmaceutically acceptable carrier or vehicle can be particulate, so that the compositions are, for example, in tablet or powder form. The carrier(s) can be liquid, with the compositions being, for example, an oral syrup or injectable liquid.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection (as described above), one or more of a surfactant, preservative, wetting agent, dispersing agent, suspending agent, buffer, stabilizer and isotonic agent can also be included.

Liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Physiological saline is a preferred adjuvant. An injectable composition is preferably sterile.

As noted above, the amount of the fucose analog that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a fucose analog such that a suitable dosage will be obtained. Typically, this amount is at least about 0.01% of a fucose analog by weight of the composition. When intended for oral administration, this amount can be varied to range from about 0.1% to about 80% by weight of the composition. Preferred oral compositions can comprise from about 4% to about 50% of the fucose analog by weight of the composition. Preferred compositions of the present invention are prepared so that a parenteral dosage unit contains from about 0.01% to about 2% by weight of the fucose analog.

For intravenous administration, the composition can comprise from about 1 to about 250 mg of a fucose analog per kg of the animal's body weight. In some embodiments, the amount administered will be in the range from about 1 to about 25 mg/kg of body weight of the fucose analog. Preferably, the amount administered will be in the range from about 4 to about 25 mg/kg of body weight of the fucose analog.

Generally, the dosage of fucose analog administered to an animal is typically about 0.1 mg/kg to about 250 mg/kg of the animals body weight. Preferably, the dosage administered to an animal is between about 0.1 mg/kg and about 20 mg/kg of the animal's body weight, more preferably about 1 mg/kg to about 10 mg/kg of the animal's body weight.

The compositions comprise an effective amount of a fucose analog such that a suitable dosage will be obtained. Typically, this amount is at least about 0.01% of a fucose analog by weight of the composition. When intended for oral administration, this amount can be varied to range from about 0.1% to about 80% by weight of the composition. Preferred oral compositions can comprise from about 4% to about 50% of the fucose analog by weight of the composition. Preferred compositions of the present invention are prepared so that a parenteral dosage unit contains from about 0.01% to about 2% by weight of the fucose analog.

For intravenous administration, the composition can comprise from about 1 to about 250 mg of a fucose analog per kg of the animal's body weight. In some embodiments, the amount administered will be in the range from about 1 to about 25 mg/kg of body weight of the fucose analog. Preferably, the amount administered will be in the range from about 4 to about 25 mg/kg of body weight of the fucose analog.

Generally, a fucose analog or a pharmaceutical composition thereof can be administered on a daily, weekly, biweekly or monthly schedule, according to the desired effect. A fucose analog or a pharmaceutical composition thereof can be administered from about 1 to 5, about 1 to about 10, about 1 to about 15, or more cycles, wherein each cycle is a month in duration. The doses within each cycle can be given on daily, every other day, twice weekly, weekly, bi-weekly, once every three weeks or monthly. A cycle may optionally include a resting period, during which fucosylation of proteins (e.g., antibodies or other proteins) increases. Alternatively, a resting period can be included between cycles. Such a resting period can allow restoration of fucosylation of proteins involved in essential functions.

The preferred mode of administration of a fucose analog, or a pharmaceutical composition thereof, is left to the discretion of the practitioner, and will depend in-part upon the site of the medical condition (such as the site of cancer or autoimmune disease). In one embodiment, the fucose analog or compositions are administered parenterally. In another embodiment, the fucose analog or compositions are administered orally.

In specific embodiments, it can be desirable to administer one or more fucose analogs or compositions locally to the area in need of treatment. This can be achieved, for example, and not by way of limitation, by local infusion during surgery; topical application; by injection; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue.

In another embodiment, administration can be by direct injection at the site (or former site) of a manifestation of an autoimmune disease.

In another embodiment, the fucose analogs can be delivered in a vesicle, in particular a liposome (see Langer, *Science* 249:1527-1533 (1990); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327; see generally ibid.).

In yet another embodiment, the fucose analogs or compositions can be delivered in a controlled release system. In one embodiment, a pump can be used (see Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). Other controlled-release systems discussed in the review by Langer (*Science* 249:1527-1533 (1990)) can be used.

The term "carrier" refers to a diluent, adjuvant or excipient, with which a fucose analog is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the fucose analogs or compositions and pharmaceutically acceptable carriers are sterile. Water is a preferred carrier when the fucose analogs are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Therapeutic Methods Using Fucose Analogs to Reduce Antibody and Other Protein Fucosylation In Vivo The fucose analogs of formulae I, II, III, IV, V and VI (hereinafter 'the fucose analogs') as provided herein are useful for treating cancer, an autoimmune disease or an infectious disease in an animal.

Treatment of Cancer

The fucose analogs are useful for treating cancer in patients. Administration of a fucose analog to an animal (e.g., a mammal, such as a human) in need thereof can result in inhibition of the multiplication of a tumor cell(s) or cancer cell(s), or treatment of cancer in an animal (e.g., a human patient). The fucose analogs can be used accordingly in a variety of settings for the treatment of animal cancers.

The fucose analogs are also useful for enhancing the in vivo production of antibodies lacking core fucosylation. Increasing the proportion of such antibodies against cancer targets in a patient can result in inhibition of the multiplication of a tumor cell(s) or cancer cell(s), or treatment of cancer in an animal (e.g., a human patient). The fucose analogs can be used accordingly in a variety of settings for the treatment of animal cancers.

Particular types of cancers that can be treated with the fucose analogs include, solid tumors and hematologic malignancies. Such cancers include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias, and (3) lymphomas such as Hodgkin's disease, non-Hodgkin's Lymphoma, multiple myeloma, Waldenstrom's macroglobulinemia, Heavy chain disease, and Polycythemia vera.

Multi-Modality Therapy for Cancer

Cancer, including, but not limited to, a tumor, a metastasis, or any disease or disorder characterized by uncontrolled cell growth, can be treated or prevented by administration of a fucose analog of any of formulae I, II, III, IV, V or VI as provided above, to an animal (e.g., a mammal, such as a human) in need thereof. In some embodiments, the invention provides methods for treating or preventing cancer, comprising administering to an animal in need thereof an effective amount of a fucose analog and optionally a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The fucose analogs can be administered to an animal that has also undergone surgery as treatment for the cancer.

In one embodiment, the additional method of treatment is radiation therapy.

In a specific embodiment, the fucose analog is administered concurrently with the chemotherapeutic agent or with radiation therapy. In another specific embodiment, the chemotherapeutic agent or radiation therapy is administered prior or subsequent to administration of a fucose analog, preferably at least an hour, five hours, 12 hours, a day, a week, two weeks, three weeks, a month, or several months (e.g., up to three months), prior or subsequent to administration of a fucose analog.

A chemotherapeutic agent can be administered over a series of sessions, and can be any one or a combination of the chemotherapeutic agents provided herein. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, the invention provides methods of treatment of cancer with a fucose analog as an alternative to chemotherapy or radiation therapy, where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

Multi-Drug Therapy for Cancer

The present invention includes methods for treating cancer, comprising administering to an animal in need thereof an effective amount of a fucose analog and a therapeutic agent that is an anti-cancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, a camptothecin, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, the anti-cancer agent includes, but is not limited to: alkylating agents, nitrogen mustards (cyclophosphamide, Ifosfamide, trofosfamide, Chlorambucil), nitrosoureas (carmustine (BCNU), Lomustine (CCNU)), alkylsulphonates (busulfan, Treosulfan), triazenes (Dacarbazine), platinum containing compounds (cisplatin, oxaliplatin, carboplatin), plant alkaloids (vinca alkaloids vincristine, Vinblastine, Vindesine, Vinorelbine), taxoids (paclitaxel, Docetaxol), DNA Topoisomerase Inhibitors, Epipodophyllins (etoposide, Teniposide, Topotecan, 9-aminocamptothecin, camptothecin), crisnatol, mitomycins (Mitomycin C); Anti-metabolites such as Anti-folates: DHFR inhibitors: methotrexate, Trimetrexate; IMP dehydrogenase Inhibitors: mycophenolic acid, Tiazofurin, Ribavirin, EICAR; Ribonucleotide reductase Inhibitors: hydroxyurea deferoxamine; Pyrimidine analogs: Uracil analogs: 5-Fluorouracil, Floxuridine, Doxifluridine, Ratitrexed; Cytosine analogs: cytarabine (ara C), Cytosine arabinoside, fludarabine; Purine analogs: mercaptopurine, Thioguanine; Hormonal therapies: Receptor antagonists: Anti-estrogen: Tamoxifen, Raloxifene, megestrol; LHRH agonists: goscrclin, Leuprolide acetate; Anti-androgens: flutamide, bicalutamide; Retinoids/Deltoids: Vitamin D3 analogs: EB 1089, CB 1093, KH 1060; Photodynamic therapies: vertoporfin (BPD-MA), Phthalocyanine, photosensitizer Pc4, Demethoxy-hypocrellin A (2BA-2-DMHA); Cytokines: Interferon-alpha, Interferon-gamma; Tumor necrosis factor: Others: Isoprenylation inhibitors: Lovastatin; Dopaminergic neurotoxins: 1-methyl-4-phenylpyridinium ion; Cell cycle inhibitors: staurosporine; Actinomycins: Actinomycin D, Dactinomycin; Bleomycins: bleomycin A2, Bleomycin B2, Peplomycin; Anthracyclines: daunorubicin, Doxorubicin (adriamycin), Idarubicin, Epirubicin, Pirarubicin, Zorubicin, Mitoxantrone; MDR inhibitors: verapamil; and $Ca^{2+}$ ATPase inhibitors: thapsigargin.

Adjuvant Therapy for Cancer

The fucose analogs can be used as an adjuvant, in combination with a cancer vaccine. The term "cancer vaccine" as used herein means a compound that selectively damages tumor cells by inducing and/or enhancing a specific immune response against the tumor cells. A cancer vaccine can be, for example, a medicament comprising a peptide, polypeptide or protein of a TAA or TSA, and pharmaceutical compositions containing a peptide, polypeptide or protein of a TAA or TSA. As used herein, TSA refers to a "tumor-specific antigen" and TAA refers to a tumor-associated antigen. TSAs are molecules unique to cancer cells. TAAs are molecules shared, but differently expressed, by cancer cells and normal cells.

The dosage of the cancer vaccine can be determined with appropriate modifications according to the extent of stimulation of an immune response against the vaccine. In general, it is between 0.01 and 100 mg/day/adult human, or preferably between 0.1 and 10 mg/day/adult human as an active principle. The cancer vaccine can be administered from once every few days to every few months. Administration can be carried out according to well-known methods for administrating a peptide, polypeptide or protein for medical use, such as subcutaneously, intravenously, or intramuscularly. In order to induce and/or enhance the immune response during administration, the peptide, polypeptide or protein can be used, in the presence or absence of an appropriate adjuvant, with or without linking to a carrier. The carrier is not limited as long as it exerts no harmful effect by itself onto the human body and is capable of enhancing antigenicity; cellulose, polymeric amino acids, albumin, and the like can be given as examples of carriers. Adjuvants can be those used in general for peptide vaccine inoculation, and a Freund incomplete adjuvant (HA), aluminum adjuvant (ALUM), *Bordetella pertussis* vaccine, mineral oil, and the like can be given as examples. In addition, the formulation can be suitably selected by applying a suitable well-known method for formulating a peptide, polypeptide or protein.

Otherwise, an effective cancer vaccine effect can be obtained also by collecting a fraction of mononuclear cells from the peripheral blood of a patient, incubating them with the peptide, polypeptide or protein of the present invention, and then returning the fraction of mononuclear cells in which induction of CTL and/or activation of CTL was observed, into the blood of the patient. A fucose analog can be co-administered during or after re-administration of the mononuclear cells. Culture conditions, such as mononuclear cell concentration, concentration of the peptide, polypeptide or proteins, culture time, and the like, can be determined by simply repeating studies. A substance having a capability to enhance the growth of lymphocytes, such as interleukin-2, may be added during culturing.

Treatment of Autoimmune Diseases

The fucose analogs are useful for modulating an autoimmune disease or for treating an autoimmune disease, so as to decrease symptoms and/or the autoimmune response. The fucose analogs can be used accordingly in a variety of settings for the treatment of an autoimmune disease in an animal.

In one embodiment, the fucose analogs down-regulate or down-modulate an auto-immune antibody associated with a particular autoimmune disease.

Particular types of autoimmune diseases that can be treated with the fucose analogs include, but are not limited to, Th2-lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed below.

Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein, Purpura Idiopathic Adrenal Atrophy, Idiopathic Pulmonary Fibrosis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis Type B, Insulin Resistance Type I Diabetes Mellitus, Ulcerative Colitis, Uveitis Vitiligo, Waldenstrom's Macroglobulinemia, and Wegener's Granulomatosis.

Multi-Drug Therapy of Autoimmune Diseases

The present invention also provides methods for treating an autoimmune disease, comprising administering to an animal (e.g., a mammal) in need thereof an effective amount of a fucose analog and optionally a therapeutic agent that known for the treatment of an autoimmune disease. In one embodiment, the anti-autoimmune disease agent includes, but is not limited to cyclosporine, cyclosporine A, mycophenylate, mofetil, sirolimus, tacrolimus, enanercept, prednisone, azathioprine, methotrexate, cyclophosphamide, prednisone, aminocaproic acid, chloroquine, hydroxychloroquine, hydrocortisone, dexamethasone, chlorambucil, DHEA, danazol, bromocriptine, meloxicam or infliximab.

Treatment of Infectious Diseases

The fucose analogs are useful for enhancing an immune response that results in increased killing or inhibition of the multiplication of a cell that produces an infectious disease or for treating an infectious disease. The fucose analogs can be used accordingly in a variety of settings for the treatment of an infectious disease in an animal.

In one embodiment, the fucose analogs enhance an immune response, resulting in kill or inhibit, or increased killing or inhibition, of the multiplication of cells that produce a particular infectious disease.

Particular types of infectious diseases that can be treated with the fucose analogs include, but are not limited to, (1) Bacterial Diseases: Diptheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococcal, Peritonitis, Bactermia Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, *Salmonella*, Typhoid Fever, Dysentery, Conjuntivitis, Sinusitis, Brucellosis, Tullaremia, Cholera, Bubonic Plague, Tetanus, Necrotizing Enteritis, Actinomycosis Mixed Anaerobic Infections, Syphilis, Relapsing Fever, Leptospirosis, Lyme Disease, Rat Bite Fever, Tuberculosis, Lymphadenitis, Leprosy, *Chlamydia*, Chlamydial Pneumonia, Trachoma, Inclusion Conjunctivitis, Systemic; (2) Fungal Diseases: Histoplamosis, Coccicidiodomycosis, Blastomycosis, Sporotrichosis, Cryptococcsis, Systemic Candidiasis, Aspergillosis, Mucormycosis, Mycetoma, Chromomycosis; (3) Rickettsial Diseases: Typhus, Rocky Mountain Spotted Fever, Ehrlichiosis, Eastern Tick-Borne Rickettsioses, Rickettsialpox, Q Fever, and Bartonellosis; (4) Parasitic Diseases: Malaria, Babesiosis, African Sleeping Sickness, Chagas Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease; (5) Viral Diseases: Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis Pericarditis, Gastroenteritis, Acquired Immunodeficiency Syndrome (AIDS), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simples Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue Lymphocytic choriomeningitis, Lassa Fever, Hemorrhagic Fever, Hantvirus, Pulmonary Syndrome, Marburg Virus Infections, Ebola Virus Infections and Smallpox.

Multi-Drug Therapy of Infectious Diseases

The present invention also provides methods for treating an infectious disease, comprising administering to an animal (e.g., a mammal) in need thereof a fucose analog and optionally a therapeutic agent that is an anti-infectious disease agent. In one embodiment, the anti-infectious disease agent is, but not limited to: (1) Antibacterial Agents: β-Lactam Antibiotics: Penicillin G, Penicillin V, Cloxacilliin, Dicloxacillin, Methicillin, Nafcillin, Oxacillin, Ampicillin, Amoxicillin, Bacampicillin, Azlocillin, Carbenicillin, Mezlocillin, Piperacillin, Ticarcillin; Aminoglycosides: Amikacin, Gentamicin, Kanamycin, Neomycin, Netilmicin, Streptomycin, Tobramycin; Macrolides: Azithromycin, Clarithromycin, Erythromycin, Lincomycin, Clindamycin; Tetracyclines: Demeclocycline, Doxycycline, Minocycline, Oxytetracycline, Tetracycline; Quinolones: Cinoxacin, Nalidixic Acid, Fluoroquinolones: Ciprofloxacin, Enoxacin, Grepafloxacin, Levofloxacin, Lomefloxacin, Norfloxacin, Ofloxacin, Sparfloxacin, Trovafloxicin; Polypeptides: Bacitracin, Colistin, Polymyxin B; Sulfonamides: Sulfisoxazole, Sulfamethoxazole, Sulfadiazine, Sulfamethizole, Sulfacetamide; Miscellaneous Antibacterial Agents: Trimethoprim, Sulfamethazole, Chloramphenicol, Vancomycin, Metronidazole, Quinupristin, Dalfopristin, Rifampin, Spectinomycin, Nitrofurantoin; Antiviral Agents: General Antiviral Agents: Idoxuradine, Vidarabine, Trifluridine, Acyclovir, Famcicyclovir, Pencicyclovir, Valacyclovir, Gancicyclovir, Foscarnet, Ribavirin, Amantadine, Rimantadine, Cidofovir; Antisense Oligonucleotides; Immunoglobulins; Inteferons; Drugs for HIV infection: Zidovudine, Didanosine, Zalcitabine, Stavudine, Lamivudine, Nevirapine, Delavirdine, Saquinavir, Ritonavir, Indinavir and Nelfinavir.

Other Therapeutic Agents

The present methods can further comprise the administration of a fucose analog and a therapeutic agent or pharmaceutically acceptable salts or solvates thereof. The fucose analog and the therapeutic agent can act additively or, more preferably, synergistically. In a preferred embodiment, a composition comprising a fucose analog is administered concurrently with the administration of one or more therapeutic agent(s), which can be part of the same composition or in a different composition from that comprising the fucose analog. In another embodiment, a fucose analog is administered prior to or subsequent to administration of the therapeutic agent(s).

In the present methods for treating cancer, an autoimmune disease or an infectious disease, the therapeutic agent also can be an antiemetic agent. Suitable antiemetic agents include, but are not limited to, metoclopromide, domperidone, proclorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinols, thiethylperazine, thioproperazine and tropisetron.

In another embodiment, the therapeutic agent can be an hematopoietic colony stimulating factor. Suitable hematopoietic colony stimulating factors include, but are not limited to, filgrastim, sargramostim, molgramostim and erythropoietin alfa.

In still another embodiment, the therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefenamic acid, nabumetone, naproxen, piroxicam and sulindac.

The invention is further described in the following examples, which are not intended to limit the scope of the invention.

EXAMPLES

Example 1

In Vivo Production of Non-Fucosylated Antibodies

Methods:

Female BALB/c mice were immunized with Keyhole Limpet Hemocyanin (KLH) 30-60 days prior to starting this study. For the first study, mice were dosed ip with 150 mg/kg of alkynyl fucose (SGD-1887), alkynyl fucose peracetate (SGD-1890), 2-fluorofucose (SGD-2083), or 2-fluorofucose triacetate (SGD-2084) daily for 7 days or were untreated. On day 2, mice were also boosted with KLH. On the day after the last ip dose, mice were terminally bled and serum obtained. For the second study, mice were given 100 mM of 2-fluorofucose (SGD-2083) in their drinking water or given untreated water for 7 days, boosted with KLH, and continued with 100 mM 2-fluorofucose containing drinking water or untreated water for 7 more days before being terminally bled. Serum was then obtained. No mice died in either study. For both studies, serum was passed over a commercial anti-KLH affinity column to obtain KLH-specific polyclonal antibodies. The flow through from the anti-KLH affinity column was passed over a commercial protein A column to obtain the remaining antibodies.

Dot blots: 0.5 µg each of antibodies from untreated and treated animals, as well as standards of antibody cAC10 having known amounts of core fucosylation (0 to 100% fucose), were blotted onto a nitrocellulose membrane. The proteins levels were visualized by Ponceau staining. The blot was probed with biotinylated *Aspergillus oryzae* L-fucose-specific lectin (AOL) (which binds to fucosylated antibodies) and developed with streptavidin HRP and ECL. Gel loading (visible) and fucose signals (bioluminescence) were measured with an Alpha Innotech camera and quantitated with the machine software.

Gas chromatography (GC): 40 µg each of the antibodies from untreated and treated animals that had been dialyzed against water, were subjected to methanolysis in methanolic HCl. Control samples of antibody cAC10 with 0 to 100% fucose were similarly treated. The resulting methylglycosides were derivatized by trimethylsilylation of the monosaccharide alcohols using a commercially available cocktail, Tri-Sil. The resulting trimethylsilyl methylglycosides were examined on a Hewlet Packard gas chromatograph with flame ionization detection using a temperature gradient on an Agilent J&W DB-1 column. The relevant peaks were identified by retention time comparison to sugar standards derivatized in parallel with the Ab samples. Peaks were integrated using the GC software. The fucose/mannose peak area ratios were used to determine the fucosylation state of the antibodies.

Results:

Study 1: FIG. 1 shows the dot blot (left side) from antibodies that did not bind to KLH, but were recovered from protein A column. Results are shown for cAC10 standards (lower dot blot, left most dashed rectangle and corresponding columns of upper dot blot), untreated control (lower dot blot, second dashed rectangle from the left and corresponding column of upper dot blot), and alkynyl fucose (SGD-1887; lower dot blot, middle dashed rectangle and corresponding column of upper dot blot), alkynyl fucose peracetate (SGD-1890, lower dot blot, second dashed rectangle from the right and corresponding column of upper dot blot), and 2-fluorofucose (SGD-2083; lower dot blot, right most rectangle and corresponding column of upper dot blot). Normalizing for loading level, the percent fucosylation is also shown in the graph on the right. On average, the fucosylation levels of the antibodies were reduced by about one third, as compared to the untreated controls.

Figure 2:
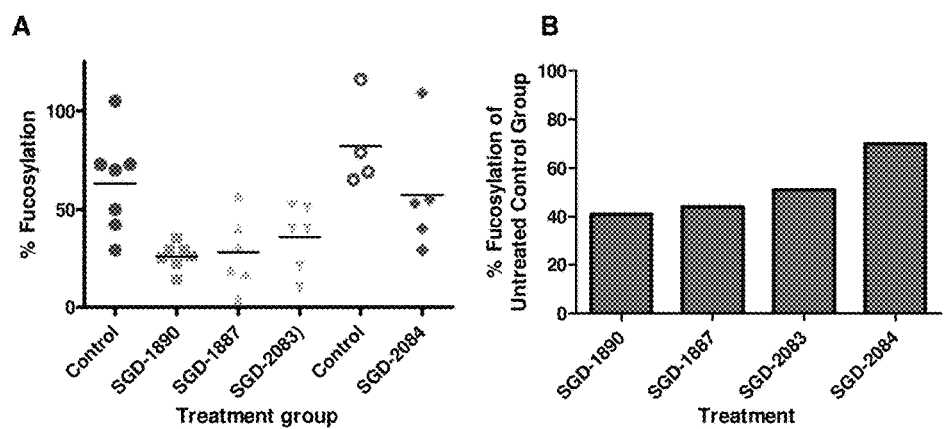
FIG. 2 shows the effects on antibody core fucosylation of administration of fucose analogs via drinking water. The graphs show % fucosylation of antibodies as a determined by gas chromatograph (GC): panels A and B show fucosylation levels of the anti-KLH antibodies (Abs) isolated from the treated groups while panels C and D show the fucosylation levels of the remaining (non-KLH-specific) IgG antibodies. Panels A and C show the percent fucosylation of each animal determined using a purified antibody standard curve (0-100% fucosylation). Panels B and D show the fucosylation level of the treated groups as a percentage of the average untreated control group value.
Figure 2:
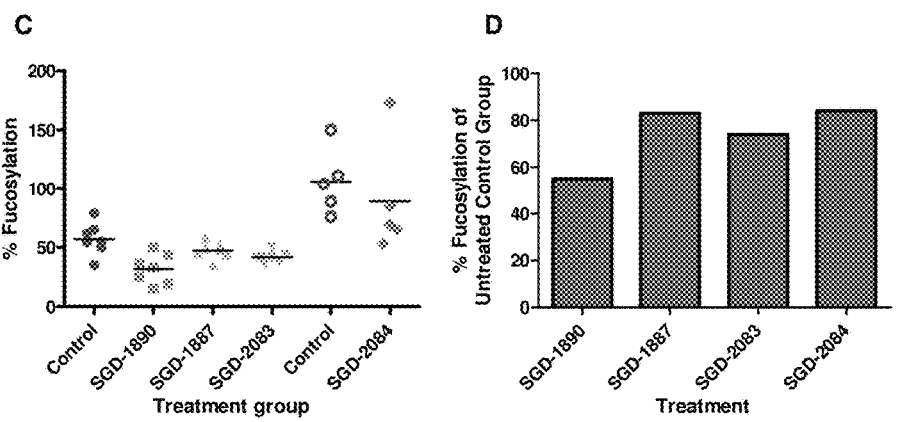

FIG. 2 shows the fucosylation levels of both the anti-KLH antibodies (panels A and B) and the remaining serum IgG molecules isolated from the treated groups (panels C and D). Fucosylation levels are shown both as percent fucosylation based on the cAC10 antibody standards (panels A and C) and the average value for the treated groups as a percentage of the average value for the untreated control group (panels B and D). On average, the fucosylation levels of the anti-KLH antibodies were reduced by about one half by treatment with three of the fucose analogs. The remaining collected antibodies also exhibited a reduction in core fucosylation of about one quarter. In this study, overall antibody levels (KLH-specific and non-specific) increased in the mice after exposure to KLH. As a result, most antibodies were newly synthesized during the treatment periods. These observations indicate that newly produced antibodies can exhibit reduced core fucosylation following administration of a fucose analog.

Figure 3:
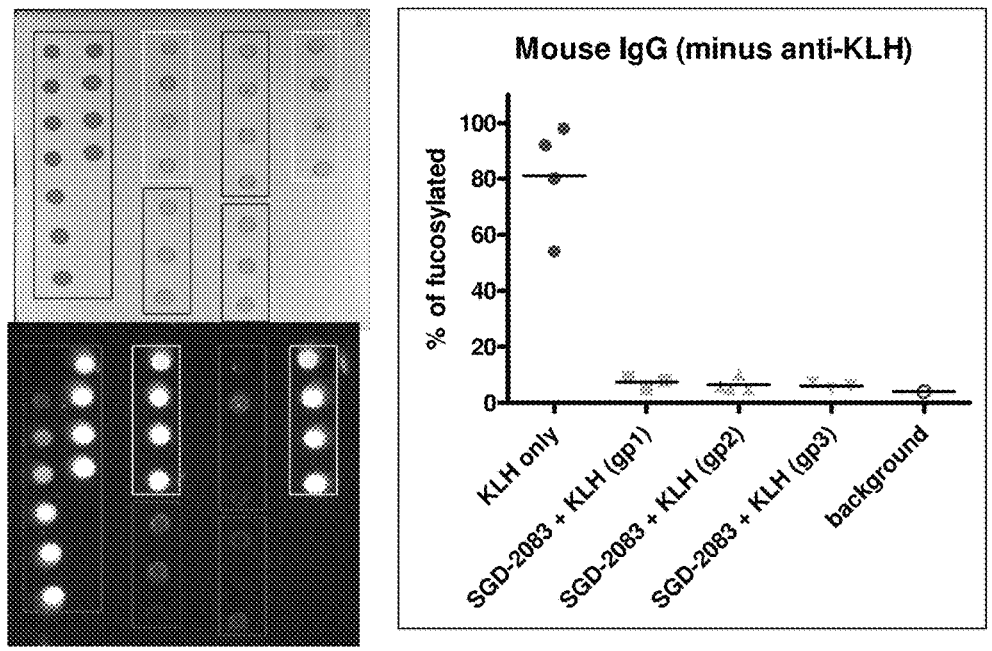
FIG. 3 shows the effects on antibody core fucosylation of administration of fucose analogs via drinking water. In this figure, fucosylation levels of the non-KLH-specific antibodies are shown. Dot blots of protein loading levels (upper left) and fucose specific bioluminescence (lower left) are shown for cAC10 standards (upper and lower dot blots, left most rectangle), untreated control (upper and lower dot blots, second from the left (upper) and right rectangles), and 2-fluorofucose (upper and lower dot blots, second from the left (lower) and second from the right rectangles (upper and lower)). After correcting for loading level, the % fucosylation is shown in the graph on the right.

Study 2: In this study, the effect of oral administration of fucose analogs was examined FIG. 3 shows the results of treatment of mice by oral administration of fucose analogs. Antibody fucosylation levels examined were those of the antibodies that did not bind to KLH, but were recovered from the protein A column. Results are shown for cAC10 standards (upper and lower dot blots, left most rectangle), untreated control (upper and lower dot blots, second from the left (upper) and right rectangles), and 2-fluorofucose (upper and lower dot blots, second from the left (lower) and second from the right rectangles (upper and lower)). Normalizing for loading level, the percent fucosylation is also shown in the graph at the right. Core fucosylation levels of antibodies from the treated animals were nearly eliminated: on average, fucosylation levels were 7% for treated and 81% for untreated animals. These observations indicate that oral administration of fucose analogs is an effective means to decrease antibody fucosylation levels.

Example 2

Activity of Fucose Analogs In Vitro in Cell Culture

Fucose analogs have been evaluated for their effect on antibody core fucosylation at concentrations of 50 µM and 1 mM generally as described in Published US Patent Application 2009-0317869. Briefly, the protocol was as follows: A CHO DG44 cell line producing a humanized IgG1 anti-CD70 monoclonal antibody, h1F6 (see International Patent Publication WO 06/113909) was cultured at $7.5 \times 10^5$ cells per mL in 2 mLs of CHO culture media at 37°, 5% $CO_2$ and shaking at 100 RPM in a 6 well tissue culture plate. Media was supplemented with insulin like growth factor (IGF), penicillin, streptomycin and either 1 mM or 50 µM of the fucose analog. On day 5 post inoculation, the culture was centrifuged at 13000 RPM for 5 minutes to pellet the cells; antibodies were then purified from supernatant.

Antibody purification was performed by applying the conditioned media to protein A resin pre-equilibrated with 1× phosphate buffered saline (PBS), pH 7.4. After washing resin with 20 resin bed volumes of 1× PBS, antibodies were eluted with 5 resin bed volumes of Immunopure IgG elution buffer (Pierce Biotechnology, Rockford, Ill.). A 10% volume of 1M Tris pH 8.0 was added to neutralize the eluted fraction. The results are shown in the following tables.

TABLE 1

| Name (Chemical name) | $R^5$ | $R^1$-$R^4$ | Inhibition at 50 µM | Inhibition at 1 mM |
|---|---|---|---|---|
| Alkynyl fucose (5-ethynylarabinose) | —C≡CH | —OH | >80% | ND |
| Alkynyl fucose peracetate Alkynyl fucose tetraacetate (5-ethynylarabinose tetraacetate) | —C≡CH | —OAc | >80% | >80% |
| 5-propynyl fucose tetraacetate (5-propynylarabinose tetraacetate) | —C≡CCH₃ | —OAc | 50% | >80% |
| propargyl fucose tetraacetate ((3S,4R,5R,6S)-6-(prop-2-ynyl)-tetrahydro-2H-pyran-2,3,4,5-tetrayl tetraacetate) | —CH₂C≡CH | —OAc | ~10% | ~10-20% |
| Peracetyl galactose (galactose pentaacetate) | —OAc | —OAc | ~0% | ~0% |
| 5-vinyl fucose tetraacetate (5-ethylenylarabinose tetraacetate) | —CHCH₂ | —OAc | ~0% | ~4% |
| 6-cyano fucose tetraacetate (6-cyanofucose tetraacetate) | —CH₂CN | —OAc | 30% | >80% |
| 5-cyano fucose tetraacetate (pyranose form) (5-cyanoarabinopyranose tetraacetate) | —CN | —OAc | 20% | ND |
| 5-cyano fucose tetraacetate (furanose form) (5-cyanoarabinofuranose tetraacetate) | —CN | —OAc | 5-10% | ND |
| 5-methylester fucose tetraacetate (5-carboxymethyl arabinose tetraacetate) | —C(O)OCH₃ | —OAc | 30% | >80% |
| 5-(CH(OAc)CH₃) peracetyl fucose (6-methylgalactose pentaacetate) | —CH(OAc)CH₃ | —OAc | ~0% | 40% |
| 5-methyloxiran-arabinose tetraacetate ((3S,4R,5S,6R)-6-((S)-2-methyloxiran-2-yl)-tetrahydro-2H-pyran-2,3,4,5-tetrayl tetraacetate) | (methyloxiranyl group) | —OAc | ~0% | ~35-40% |
| 6-iodo-fucose tetraacetate (6-iodofucose tetraacetate) | —CH₂I | —OAc | 3% | 30% |
| 6-chloro-fucose tetraacetate (6-chlorofucose tetraacetate | —CH₂Cl | —OAc | 20% | 20-30% |
| 6-bromo-fucose tetraacetate (6-bromofucose tetraacetate) | —CH₂Br | —OAc | 50% | 80% |
| Alkynyl fucose tetrapropanonate (5-ethynylarabinose tetrapropanoate) | —C≡CH | —OC(O)CH₂—CH₃ | >80% | >80% |
| Alkynyl fucose tetra-n-hexanoate (5-ethynylarabinose tetrahexanoate) | —C≡CH | —OC(O)(CH₂)₄—CH₃ | >80% | >80% |

TABLE 1-continued

| Name (Chemical name) | $R^5$ | $R^1$-$R^4$ | Inhibition at 50 µM | Inhibition at 1 mM |
|---|---|---|---|---|
| Alkynyl fucose tetrakis(trimethylacetate) (5-ethynylarabinose tetra(trimethylacetate)) | —C≡CH | —OC(O)C(CH$_3$)$_3$ | 20% | 60% |
| Alkynyl fucose tetrakis(trimethylacetate) (5-ethynylarabinose tetra(trimethylacetate)) | —C≡CH | —OC(O)C(CH$_3$)$_3$ | 5% | 10% |
| Alkynyl fucose 1,2,3-(trimethylacetate) (5-ethynylarabinose 1,2,3-(trimethylacetate)) | —C≡CH | —OC(O)C(CH$_3$)$_3$ and —OH | ~0% | ND |
| Alkynyl fucose di(trimethylacetate) (5-ethynylarabinose 1,3-(trimethylacetate)) | —C≡CH | —OC(O)C(CH$_3$)$_3$ and —OH | >80% | ND |
| Alkynyl fucose pernicotinate | —C≡CH | —C(O)-3-pyridyl | >80% | >80% |
| Alkynyl fucose perisonicotinate | —C≡CH | —C(O)-4-pyridyl | >80% | >80% |
| Alkynyl fucose per-PEG ester | —C≡CH | —C(O)—(CH$_2$CH$_2$O)$_2$—OCH$_3$ | >80% | >80% |
| 1-methyl-2,3,4-triacetyl alkynyl fucose | —C≡CH | $R^1$ = OCH$_3$ $R^2$, $R^3$, $R^4$ = OAc | 68% | >80% |
| Alkynyl fucose perisobutanoate | —C≡CH | —OC(O)CH(CH$_3$)$_2$ | >80% | >80% |

"ND" means not detected due to poor antibody production or inhibition of cell growth in the presence of the fucose analog.

TABLE 2

| Name (Chemical name) | $R^5$ | $R^1$ | $R^2$/$R^{2a}$ | $R^3$/$R^{3a}$ | Inhibition at 50 µM | Inhibition at 1 mM |
|---|---|---|---|---|---|---|
| 2-deoxy-2-fluorofucose diacetate ($R^4$ = OAc) | —CH$_3$ | —OH | —F/—H | —OAc/—H | >80% | >80% |
| 2-deoxy-2-chlorofucose triacetate ($R^4$ = OAc) | —CH$_3$ | —OAc | —Cl/—H | —OAc/—H | 17% | >80% |
| Allene ($R^4$ = OAc) | —CH=C=CH$_2$ | —OAc | —OAc/—H | —OAc/—H | 23% | 34% |
| 2-deoxy-2-fluorofucose ($R^4$ = OH) | —CH$_3$ | —OH | —F/—H | —OH/—H | >80% | >80% |
| 2-deoxy-2-fluorofucose peracetate ($R^4$ = OAc) | —CH$_3$ | —OAc | —F/—H | —OAc/—H | >80% | >80% |
| 1,2-difluoro-1,2-didexoy fucose peracetate ($R^4$ = OAc) | —CH$_3$ | —F | —F/—H | —OAc/—H | >80% | >80% |
| 6,6-difluorofucose tetraacetate ($R^4$ = OAc) | —CHF$_2$ | —OAc | —OAc/—H | —OAc/—H | >80% | >80% |
| 2-deoxy-2,2-difluorofucopyranose triacetate (alpha) ($R^4$ = OAc) | —CH$_3$ | —OAc | —F/—F | —OAc/—H | 0 | 64% |
| 2-deoxy-2,2-difluorofucopyranose triacetate (beta) ($R^4$ = OAc) | —CH$_3$ | —OAc | —F/—F | —OAc/—H | 0 | 75% |
| 6-methyl-tetrahydro-2H-pyran-2,4,5-triyl triacetate ($R^4$ = OAc) | —CH$_3$ | —OAc | —H/—H | —OAc/—H | 0 | 36% |
| 5-Benzyloxy fucose peracetate ($R^4$ = OAc) | —CH$_2$OCH$_2$Ph | —OAc | —OAc/—H | —OAc/—H | 0 | 75% |

"ND" not detected due to poor antibody production or inhibition of cell growth in the presence of the fucose analog.

Certain other fucose analogs were tested for their ability to be incorporated into antibodies. These fucose analogs were tested at concentrations of 50 μM and 1 mM using the methodology as described above. The results are shown in the following table.

TABLE 3

| Name (Chemical name) | $R^5$ | $R^1$-$R^4$ | % Incorporation |
|---|---|---|---|
| Propargyl fucose or (3S,4R,5R)-6-(prop-2-ynyl)tetrahydro-2H-pyran-2,3,4,5-tetrayl tetraacetate | (propargyl) | —OAc | 80% (1 mM) |
| 5-(Z)-propenyl fucose peracetate | (Z-propenyl) | —OAc | ~30% |
| Isopropenyl peracetyl fucose or (3S,4R,5R,6S)-6-(prop-1-en-2-yl)-tetrahydro-2H-pyran-2,3,4,5-tetrayl tetraacetate | (isopropenyl) | —OAc | >80% (1 mM and 50 uM) |
| 5-ethyl fucose or (3S,4R,5S,6S)-6-ethyl-tetrahydro-2H-pyran-2,3,4,5-tetraol | —CH$_2$CH$_3$ | —OH | >80% (1 mM and 50 uM) |
| 5-ethyl fucose peracetate or (3S,4R,5S,6S)-6-ethyl-tetrahydro-2H-pyran-2,3,4,5-tetrayl tetraacetate | —CH$_2$CH$_3$ | —OAc | >90% (1 mM and 50 uM) |
| 5-cyclopropyl fucose or (3S,4R,5S,6S)-6-cyclopropyltetrahydro-2H-pyran-2,3,4,5-tetraol | (cyclopropyl) | —OH | ~80% |
| 5-cyclopropyl fucose peracetate or (3S,4R,5R,6S)-6-cyclopropyltetrahydro-2H-pyran-2,3,4,5-tetrayl tetraacetate | (cyclopropyl) | —OAc | ~80% |
| 5-propyloxyarabinose tetraacetate or (3S,4R,5S,6R)-6-((S)-2-methyloxiran-2-yl)tetrahydro-2H-pyran-2,3,4,5-tetrayl tetraacetate | (methyloxiranyl) | —OAc | ~60% |
| Fluoromethylene fucose or (3S,4R,5S)-6-(fluoromethyl)tetrahydro-2H-pyran-2,3,4,5-tetrayl tetraacetate | —CH$_2$F | —OAc | >90% (1 mM and 50 μM) |
| 5-chloromethylene peracetyl fucose or (3S,4R,5S)-6-(chloromethyl)tetrahydro-2H-pyran-2,3,4,5-tetrayl tetraacetate | —CH$_2$Cl | —OAc | ~80% |

TABLE 3-continued

| Name (Chemical name) | $R^5$ | $R^1$-$R^4$ | % Incorporation |
|---|---|---|---|
| 5-bromomethylene peracetyl fucose or (3S,4R,5S)-6-(bromomethyl)tetrahydro-2H-pyran-2,3,4,5-tetrayl tetraacetate | —CH$_2$Br | —OAc | ~50% (50 uM; 20% at 1 mM) |
| 5-iodomethylene-peracetyl fucose or (3S,4R,5S)-6-(iodomethyl)tetrahydro-2H-pyran-2,3,4,5-tetrayl tetraacetate | —CH$_2$I | —OAc | ~30% |
| Azido peracetyl fucose or (3S,4R,5R)-6-(azidomethyl)tetrahydro-2H-pyran-2,3,4,5-tetrayl tetraacetate | —CH$_2$N$_3$ | —OAc | 60% |
| 5-(2-azidoethyl) arabinose tetraacetate or (3S,4R,5R,6S)-6-(2-azidoethyl)tetrahydro-2H-pyran-2,3,4,5-tetrayl tetraacetate | —CH$_2$CH$_2$N$_3$ | —OAc | 20% |
|  | —CH=C=CH$_2$ | —OAc | ~30% |
| Isopropyl peracetyl fucose or (3S,4R,5R,6S)-6-isopropyltetrahydro-2H-pyran-2,3,4,5-tetrayl tetraacetate | Isopropyl | —OAc | Not detected |

These assays identified candidate compounds for inhibition of core antibody fucosylation in mammals.

Example 3

Production of Non-fucosylated Antibodies In Vivo Following Oral Administration

In this study, the effects of oral administration of the fucose analog 2-fluorofucose (SGD-2083) were further examined Female BALC/c mice were offered 1, 10 and 100 mM 2-fluorofucose in their drinking water for 14 days. Mice were immunized with TiterMAX Classic and offered 1, 10 and 100 mM 2-fluorofucose in their drinking water for an additional 7 days. Mice were then terminally bled and serum obtained. Endogenous antibodies were purified by passing the serum over a protein A column.

Figure 4:
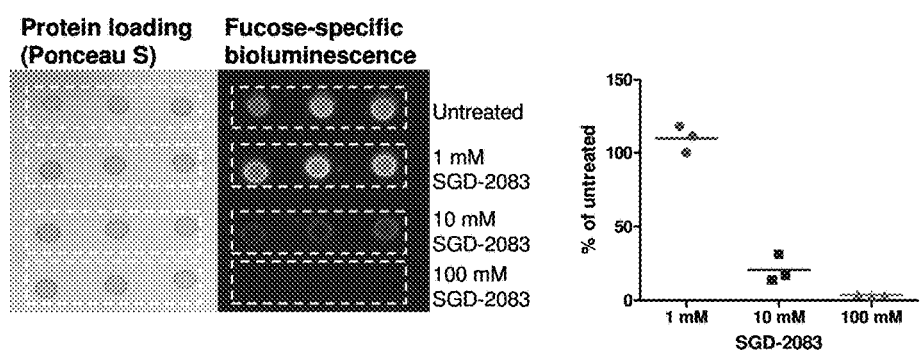
FIG. 4 shows the effects of different doses of 2-fluorofucose, administered via drinking water, on antibody core fucosylation. The dot blots show protein loading levels (left) and fucose specific bioluminescence (middle) for untreated control and 1, 10, and 100 mM SGD-2083 (as indicated). The % fucosylation compared to untreated is shown in the graph on the right.

The collected antibodies were evaluated for fucosylation levels by dot blot as follows. Antibodies from untreated and treated animals (0.5 μg each), as well as standards of cAC10 with 0 to 100% fucose (only study 1), were blotted onto a nitrocellulose membrane. The proteins levels were visualized with Ponceau S. The blot was probed with biotinylated AOL lectin and developed with streptavidin HRP and ECL (as described above). Gel loading (visible) and fucose signals (bioluminescence) were measured with an Alpha Innotech camera and quantitated with the machine software.
Results:
There was a dose-dependent decrease in fucosylation levels of antibodies over the three concentrations of 2-fluorofucose (SGD-2083). Referring to FIG. 4, antibody fucosylation levels were highest in the untreated control and 1 mM 2-fluorofucose groups (left and middle panels, upper two rectangles). Antibodies from the intermediate concentration of 2-fluorofucose were nearly as depleted of fucose as the high concentration of 100 mM 2-fluorofucose. These results confirm that administration of 2-fluorofucose to mice can inhibit core antibody fucosylation.

Example 4

Affects of Fucose Analogs on Human Cells

The ability of different fucose analogs to inhibit the fucosylation of IgG antibodies produced by human myeloma cells as well as the fucosylation of surface proteins of human cancer cell lines was investigated. In a first study, the ability of fucose analogs to inhibit fucosylation of IgG produced by the cell line LP-1, a human multiple myeloma cell line, was investigated. The antibodies produced by, and found in the culture medium of, untreated LP-1 cells were confirmed to be of the IgG type by western blot using anti-human IgG detection (data not shown). This was accomplished by growing 20 mL of LP-1 cells in a T-75 culture flask (250,000 cells/mL) for 5 days at 37° C. in a humidified atmosphere of 5% $CO_2$ in IgG-depleted tissue culture media (90% RPMI with 10% IgG-depleted heat inactivated FBS). Harvest of the cells was by centrifugation (200×g, 4° C., 5 min), and the culture medium was collected. The medium was filtered through a 0.22 μm filter and then incubated with 1 mL of a 50% MabSelect™ protein A resin slurry in PBS at 4° C. with rotation overnight to capture the IgG. The resin slurry was allowed to settle and most of the medium was removed. The resin slurry was transferred with ~0.5 mL media to two cellulose acetate filter spin cups and was centrifuged at 5000×g for 1 mm. The resin bed was then washed 3 times with 0.5 mL PBS. The IgG was eluted with 700 μL of Pierce IgG elution buffer (into with 52 μL of 9 M Tris buffer, pH 9.5 to adjust the pH after elution). The resulting elution was transferred to a 10,000 MW cutoff centrifugal concentrator and the sample was concentrated to approximately 20 μL. 1 μL of the concentrated sample was loaded on an SDS polyacrylamide gel for separation followed by blotting onto nitrocellulose membrane. Staining of the blot for total protein was with Ponceau S and for identification of isotype with anti-human IgG antibody. The total protein stain showed bands consistent with molecular weights of IgG heavy and light chains and the anti-human IgG stain showed reaction with the protein band consistent with the molecular weight of heavy chain as expected.

Antibody fucosylation can also be determined using a biotin-labeled *Aspergillus oryzae* L-fucose-specific lectin (AOL), which binds specifically to the α-1,6-linked fucose of the antibody. This method for fucose detection works for both blotted protein that has either been separated by SDS-PAGE or for protein that has been applied to nitrocellulose without separation. The fluorescent signal generated using the AOL-biotin conjugate with streptavidin-HRP binding and ECL detection can be quantitated using an Alpha Innotech FlourChem® Q system. The IgG isolated from LP-1 culture displayed an AOL-dependent signal in the band corresponding to the MW of the heavy chain as expected (data not shown). The analogs 2-fluorofucose (SGD-2083) and 2-fluorofucose peracetate (SGD-2084) did not inhibit fucosylation of antibody, but alkynyl fucose peracetate (SGD-1890) did.

To further evaluate the activities of different fucose analogs, 48 different fucose analogs and other four glycosylation inhibitors were tested for their ability to affect the fucosylation the LP-1-generated IgG. LP-1 cells (250,000 cells/mL, 3 mL per compound in 6-well plates) were incubated with 100 μM of each fucose analog for 5 days at 37° C. with a humidified atmosphere of 5% $CO_2$ in IgG-depleted tissue culture media (90% RPMI with 10% IgG-depleted heat inactivated FBS). The IgG was isolated as described above using only 0.5 mL of MabSelect™ protein A resin slurry and one spin cup per sample with elution in 400 μL of IgG elution buffer into 25 μL of 9 M Tris buffer, pH 9. The eluates were concentrated to 10-20 μL per sample and 2 μL of each of the concentrated eluates were dotted onto a nitrocellulose membrane and stained with Ponceau S to estimate and adjust the sample loading for AOL staining. From this estimation of total protein in each sample, approximately 0.5 μg of each sample was dotted onto the membrane, air-dried, and stained with Ponceau S. An image of this stained membrane was captured using an Alpha Innotech FlourChem® Q system. The membrane was then blocked with 5% Bovine Serum Albumin (BSA) in Tris Buffered Saline (TBS) for 1 hr, washed with TBST (TBS with Triton) 3 times and then incubated with 5 μg/ml biotinylated-AOL for 1 hr. The membrane was washed again with TBST 3 times, followed by Streptavidin-HRP incubation for 30 mm and final washes with TBST 3 times. The bioluminescent signal was revealed using chemiluminescence reagents (ECL) and was analyzed using an Alpha Innotech FlourChem® Q system and Alphaview® software. The results are shown in the following table. For some analogs, multiple samples were analyzed, as indicated in the table.

TABLE 4

| Molecule Namee | SGD number | % of control fucosylated IgG value |
|---|---|---|
| alkynyl fucose | 1887 | 3 |
| alkynyl fucose peracetate | 1890 | 0; 0.08; 2 |
| 5-vinyl fucose tetraacetate | 1922 | 2 |
| 5-cyanomethylene fucose tetraacetate | 1924 | 96 |
| L-galactono-1,4-lactone | 1931 | 81 |
| Methyl a-L-fucopyranoside | 1932 | 87 |
| 5-propynyl fucose tetraacetate | 1937 | 315 |
| 5-(Z)-propenyl fucose peracetate | 1944 | 72 |
| 6-propargylamino fucose | 1950 | 40 |
| 5-methyl ester fucose tetraacetate | 1959 | 94 |
| castanospermine | 1960 | 300 |
| 5-methylketo fucose tetraacetate | 1964 | 5 |
| 6-bromo fucose tetraacetate | 1969 | 1 |
| 5-isopropyl fucose tetraaceate | 1977 | 79 |
| Kifunensine | 1978 | 0.44; 2 |
| propargyl fucose tetraacetate | 1987 | 38 |
| 6-fluoro fucose tetraacetate | 1988 | 15 |
| 5-ethyl fucose tetraacetate | 1989 | 11 |
| 5-carboxamido fucose tetraacetate | 1995 | 79 |
| 6-alkyne-6-acetoxy fucose tetraacetate | 2004 | 29 |
| alkynyl fucose tetrapropionate | 2010 | 1.5 |
| alkynyl fucose tetrahexanoate | 2012 | 67 |
| 5-epoxy fucose tetraacetate | 2020 | 5 |
| 6-thio galactose pentaacetate | 2025 | 44 |
| 1-methyl fucose triacetate | 2039 | 1 |
| alkynyl fucose tetraisobutanoate | 2043 | 34 |
| 6-formyl fucose tetraacetate | 2045 | 70 |
| 6'6-difluoro fucose tetraacetate | 2046 | 2 |
| alkynyl fucose tetranicotinate | 2047 | 50 |
| benzyloxy fucose tetraacetate | 2048 | 114 |
| alkynyl fucose tetra PEG ester | 2057 | 64 |
| alkynyl fucose tetraisonicotinate | 2058 | 34 |
| 1-methyl alkynyl fucose triacetate | 2059 | 89 |
| 6-carboxymethyl ester fucose tetraacetate | 2061 | 71 |
| 6-keto-6-ethyl fucose tetraacetate | 2067 | 3 |
| 5-(2-cyanoethyl)arabinose tetraacetate | 2070 | 51 |
| D-galactose pentaacetate | 2074 | 118 |
| 1,2-dideoxy-1,2-dehydro fucose diacetate | 2080 | 159 |
| 1-deoxy fucose triacetate | 2081 | 70 |
| 1,2-difuloro fucose diacetate | 2082 | 87 |

TABLE 4-continued

| Molecule Namee | SGD number | % of control fucosylated IgG value |
|---|---|---|
| 2-fluoro-2-deoxy fucose | 2083 | 66 |
| 2-fluoro-2-deoxy fucose tetraacetate | 2084 | 52 |
| 6-allene fucose tetraacetate | 2097 | 45 |
| 2-chloro-2-deoxy fucose tetraacetate | 2099 | 146 |
| 2-deoxy fucose triacetate | 2108 | 104 |
| 3-thio fucose tetraacetate | 2112 | 64 |
| 6-deoxy-L-talose | 2113 | 93 |
| 4-deoxy fucose triacetate | 2134 | 49 |

Three fucose analogs were chosen for a full SDS-PAGE/Western blot analysis to show that changes in the fucose signal on the heavy chain can be detected by this technique. The three analogs chosen were used at a concentration of 50 µM. These analyses compared the activity of 2-fluorofucose (SGD-2083), 2-fluorofucose peracetate (SGD-2084), and alkynyl fucose peracetate (SGD-1890) with antibody from untreated cells. Use of alkynyl fucose peracetate produced IgG that did not show reactivity with the biotinylated AOL, confirming that changes in AOL signal can be detected by this method while 2-fluorofucose (SGD-2083) and 2-fluorofucose peracetate (SGD-2084) showed no apparent change in the AOL signal. These results are generally consistent with the results for these compounds in Table 4.

Many of the fucose analogs tested in Table 4 appeared to decrease fucosylation of antibody produced by human myeloma cells. The dot blots of the compounds showed that 10 of them were potentially strong inhibitors of IgG fucosylation in human cells, using decrease in AOL signal as an indication of inhibition. These fucose analogs are alkynyl fucose peracetate (SGD-1890), alkynyl fucose tetrapropionate (SGD-2010), 1-methyl fucose triacetate (SGD-2039), 5-ethyl fucose tetraacetate (SGD-1989), 6-fluoro fucose tetraacetate (SGD-1988), 6-bromo fucose tetraacetate (SGD-1969), 6'6-difluoro fucose tetraacetate (SGD-2046), 6-keto-6-ethyl fucose tetraacetate (SGD-2067), 5-epoxy fucose tetraacetate (SGD-2020), and 5-methylketo fucose tetraacetate (SGD-1964).

To further define the results of the AOL dot blot, samples of the IgGs produced by cells treated with the following fucose analogs (that gave moderate to strong decreases in the dot blot AOL signal) were isolated and examined by reducing PLRP-MS to verify the fucosylation status using the MW of the heavy chain: alkynyl fucose peracetate; 5-vinylfucose tetraaceate; 5-methylketofucose tetraacetate; 6-bromofucose tetraacetate; 6-fluorofucose tetraacetate; 5-ethylfucose tetraacetate; 5-epoxyfucose tetraacetate; 6'6-difluorofucose tetraacetate; 6-keto-6-ethyl fucose tetraacetate; and 2-fluorofucose peracetate.

40 mL samples of LP-1 cells (250,000 cells/mL) were treated with 100 µM of a fucose analog for 5 days as described above, and the IgGs were purified as described using protein A resin. The yields were estimated by UV spectroscopy assuming an extinction coefficient of 1.4 AU/(mg/mL). Seven of the ten compounds yielded enough IgG to perform the analysis (use of SGD-2067, SGD-1964, and SGD-2020 yielded <10 µg of IgG, likely due to toxicity of the analogs to the cells). The remaining IgGs were reduced with 10 mM DTT at 37° C. for 15 mm and were separated on PLRP followed by MS analysis using a QTOF mass spectrometer. The resulting heavy chain peaks were examined and compared to the IgG generated by untreated cells.

The mass spectrometry results are shown in Table 5 (below). The mass spectrometry signals were evaluated by comparing the peak height of the heavy chain versus heavy chain minus fucose and heavy chain minus fucose plus the mass of the fucose analog (which would arise if there was incorporation of the analog into the antibody carbohydrate). Four of the ten compounds tested were partial or full inhibitors of 1,6-fucosylation on the antibody. Alkynyl fucose peracetate (SGD-1890) provided complete inhibition while 2-fluorofucose peracetate (SGD-2084) was next best with 70% inhibition followed by 6'6-difluorofucose tetraacetate (SGD-2046) and 6-bromofucose tetraacetate (SGD-1969) with 33 and 20% inhibition mixed with incorporation of the analog into the carbohydrate.

TABLE 5

Results of PLRP-MS vs. dot blot for LP-1-generated IgG

| SGD number | PLRP/MS (inhibition or incorporation) | dot blot results (% fucose signal of control) |
|---|---|---|
| Untreated | Control | 100 |
| SGD-1890 | Full inhibitor | ~1 |
| SGD-1922 | Full incorporator | 2 |
| SGD-1964 | Not determined | 5 |
| SGD-1969 | Partial incorporator and 20% fucose inhibitor | 1 |
| SGD-1988 | Full incorporator | 15 |
| SGD-1989 | Fully incorporated | 11 |
| SGD-2020 | Not determined | 5 |
| SGD-2046 | Partial incorporator and 33% fucose inhibitor | 2 |
| SGD-2067 | Not determined | 3 |
| SGD-2084 | 70% inhibitor | 52 |

Example 5

Affects of Fucose Analogs on Protein Fucosylation

The effects of the four partial to full inhibitors, alkynyl fucose peracetate (SGD-1890), 2-fluorofucose peracetate (SGD-2084), 6'6-difluorofucose tetraacetate (SGD-2046), and 6-bromofucose tetraacetate (SGD-1969), on protein cell surface fucosylation was tested for human cancer cells by incubation of five different human-derived cancer cell lines (Caki-1, PC-3, Ramos, LS174t, and HL60cy). 100 µM of each inhibitor was used under standard culture conditions for approximately 1-2 weeks with regular changes of culture medium including fresh inhibitor. After the incubation period, the cells were analyzed by FACS using four different detection reagents: biotinylated-Lens culimaris agglutinin-A (LCA), anti-Lewis$^x$ antibody (anti-SSEA1), an anti-Lewis$^y$ antibody (cBR96), and a Recombinant Human P-Selectin/CD62P/Fc Fusion protein. The procedure involved washing of the cells with FACS buffer (PBS+10% bovine serum albumin+0.02% sodium azide) 3 times followed by incubation with the primary detection reagent for 1 hr at 4° C., followed by 3 washes with FACS buffer and then incubation with the secondary detection reagent for 1 hr at 4° C. The cells were finally washed with FACS buffer 3 times and resuspended in FACS buffer and examined using a BD FACScan instrument. The LCA reagent recognizes sequences containing α-linked mannose residues and its affinity is markedly enhanced by α-linked fucose residues attached to the N-acetylchitobiose portion of the core oligosaccharide. The P-selectin fusion protein detects P-selectin ligand present on the surface of cells, an interaction which involves the sialyl Lewis$^x$ epitope present of the P-selectin ligand.

All of the cell lines examined showed staining with the LCA reagent, which recognizes sequences containing α-linked mannose residues, the affinity of which is markedly enhanced by α-linked fucose residues attached to the N-acetylchitobiose portion of the core oligosaccharide. The LCA detection of this sugar epitope was decreased upon treatment of the cells with all of the inhibitors (100 μM). This suggests that the overall presence of fucose on the cell surface is affected by treatment with the six fucose analogs examined.

Figure 7:
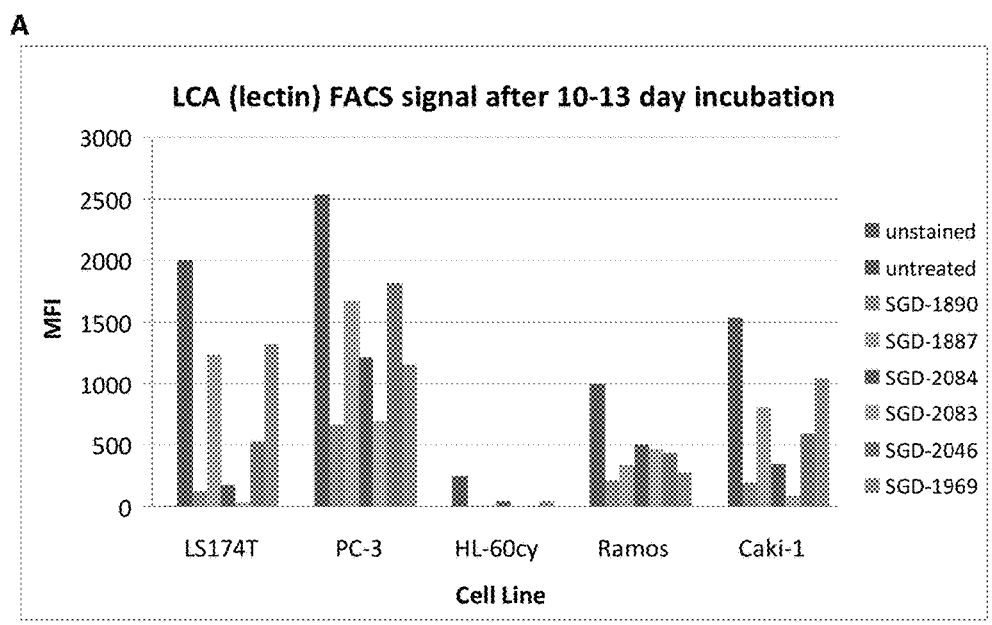
FIG. 7 shows the effects on protein fucosylation for cell lines cultured with certain fucose analogs. The LS174T, PC-3, Ramos, HL-60cy and Caki-1 cell lines were examined. Effects on LCA (lectin), Anti-SSEAI (Lewis X), cBR96 (Lewis Y), and P-Selectin (Selectin Ligand) of these cell lines, are shown in panels A-D, respectively.
Figure 7:
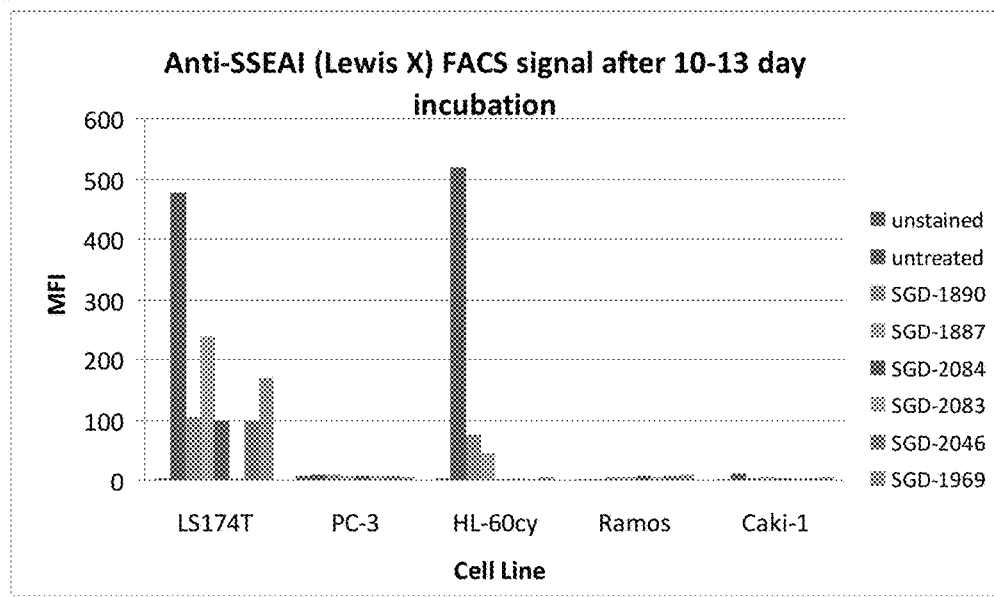
Figure 7:
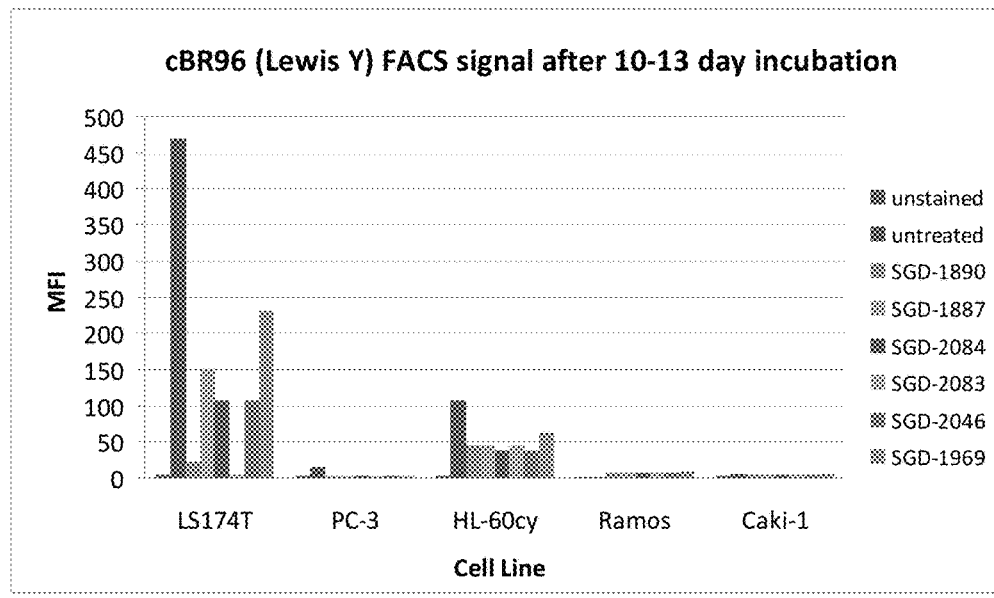
Figure 7:
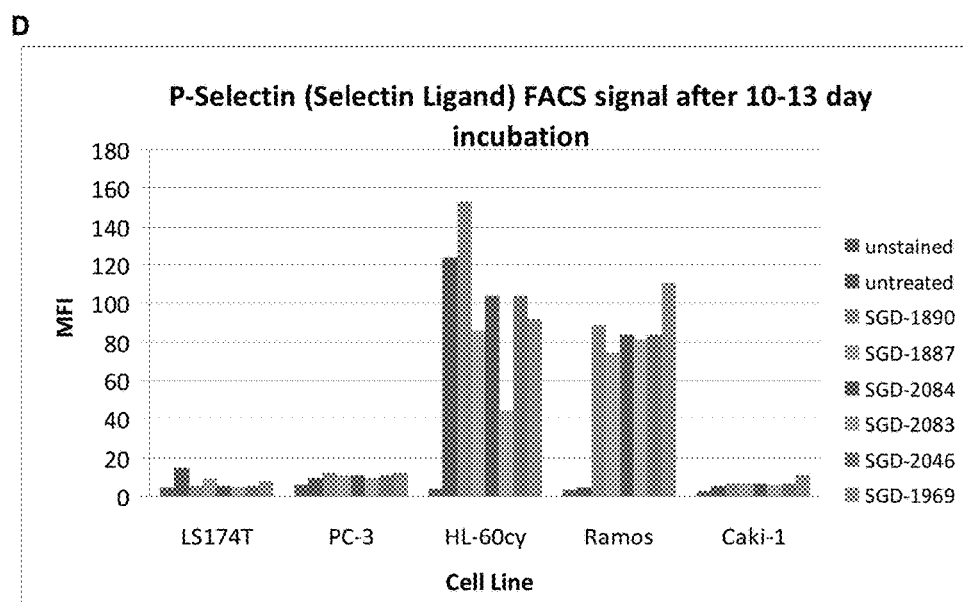

FIG. 7 shows the results of these studies. For Lewis$^X$, of the cell lines examined only untreated LS1745t and HL60cy had significant Lewis$^X$ detected on the cell surface (anti-SSEAI staining) (FIG. 7A). The anti-SSEAI detection of this structure was significantly decreased upon treatment of the cells with all of the fucose analogs (100 μM).

For Lewis$^Y$, of the cell lines examined, only untreated LS1745t and HL60cy had significant Lewis Y detected on the cell surface (cBR96 staining) (FIG. 7B). The cBR96 detection of this structure was significantly decreased upon treatment of the cells with all of the fucose analogs (100 μM).

For P-selectin, of the cell lines examined, only untreated HL60cy had significant P-selectin ligand detected on the cell surface. The detection of this ligand was decreased somewhat by treatment of the cells with all fucose analogs, except for alkynyl furocse peracetate (SGD-1890) (100 μM) (FIG. 7C). Untreated Ramos cells showed little P-selectin ligand; however, upon treatment with the fucose analogs the signal for this ligand increased. This is unusual and was not observed with previous treatment of these cells with 2-fluorofucose (SGD-2083) or alkylnyl fucose (SGD-1887).

The results suggest that treatment with these fucose analogs can affect the presence of fucose on the cell surface in general and also specifically the fucosylation of Lewis X and Lewis Y modifications on the cell surface and sialyl LewisX present on the P-selectin ligand.

Example 6

Leukocytosis and Decreased E-selectin Binding Following Oral Dosing of 2-fluorofucose The effects of a fucose analog on leukocytosis and E-selectin binding were examined in mice. Female Balb/c mice were given oral 2-fluorofucose (SGD-2083) in the drinking water or left untreated. Mice were bled prior to dosing and then weekly for three weeks to assess circulating cell numbers and their ability to bind E-selectin. In one study, 2-fluorofucose was formulated at 1 mM, 10 mM or 100 mM in the drinking water (n=3 per group). At day 14, mice were treated with TiterMAX® Classic adjuvant (Sigma) to stimulate polyclonal, antigen non-specific antibody production by B cells, and remained on the 2-fluorofucose-containing water through day 21. In a second study, mice were given oral 2-fluorofucose formulated at 10 mM and 100 mM in the drinking water for three weeks without any other treatments (n=6). On day 21, a pool of lymph nodes (axillary, brachial, superficial inguinal, and mesenteric) from each of three animals was assessed in addition to blood. Lymph nodes were homogenized into single cell suspensions, and total cell numbers were determined by counting on a hemcytometer, using Trypan Blue for dead cell exclusion. To determine total white cell numbers/μL blood, samples of blood from individual animals were counted on a hemacytometer, using Turk's solution (0.01% gentian violet in 3% acetic acid) to exclude red blood cells (RBCs). RBCs were eliminated from the remainder of the blood by osmotic lysis for flow cytometric analysis. Cells were incubated with anti-Gr-1-FITC antibodies (BD Biosciences) to identify neutrophils, and a recombinant E-selectin-human Fc fusion protein (R&D Systems). Cells were washed and then incubated with a PE-labeled goat anti-human IgG-Fc secondary antibody (Jackson Immunoresearch) to detect bound E-selectin. Samples were collected on a FACSCalibur flow cytometer and analyzed using CellQuest software. The percentage of Gr-1+ cells was determined and absolute number of neutrophils was calculated using the total white cell number from the hemacytometer count. In addition, flow samples were gated for Gr-1+ cells to assess E-selectin binding to neutrophils by histogram analysis. The geometric mean of the E-selectin fluorescent signal was determined from the histogram.

Results

Figure 5:
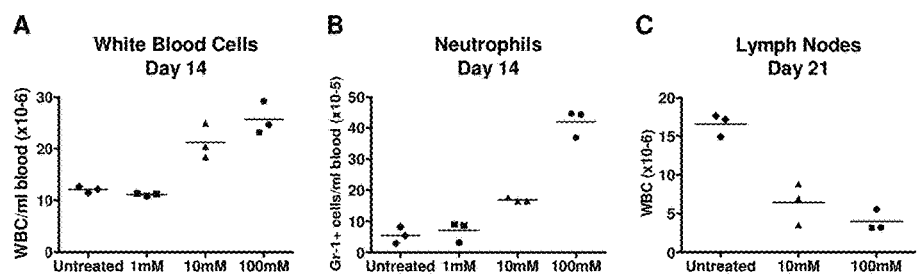
FIG. 5 shows the effects of administration of 2-fluorofucose) on circulating white blood cells and neutrophils. Panel A. Blood samples were collected from individual mice, and the white cell count was determined by counting on a hemacytometer using Turk's solution of exclude red blood cells. Panel B. To determine neutrophil counts, the percentage of white blood cells that were Gr-1+ was determined by flow cytometry and applied to the total cell count determined in (A). Panel C. A pool of lymph nodes was collected from individual mice, single cell suspensions were prepared and cells were counted on a hemacytometer. Symbols represent individual mice (n=3 per group; diamonds, untreated; squares, 1 mM 2-fluorofucose (SGD-2083); triangles, 10 mM 2-fluorofucose; circles, 100 mM 2-fluorofucose).

The results in FIGS. 5A and 5B show that oral administration of 2-fluorofucose (SGD-2083) resulted in an increase in circulating white blood cells and neutrophils, in a dose-dependent manner 2-fluorofucose given at 1 mM had very little effect, whereas increasing effect was observed with increasing doses of 10 mM and 100 mM 2-fluorofucose. The data shown in FIGS. 5A and 5B are from the first study, day 14. Similar results were obtained at days 7 and 21 in the first study as well as days 7, 14, and 21 in the second study (data not shown). Lymph nodes were also assessed at day 21 in the second study and FIG. 5C shows that oral administration of 2-fluorofucose results in a marked decreased in cellularity in the lymph nodes. The effect was more severe at 100 mM compared to 10 mM.

Figure 6:
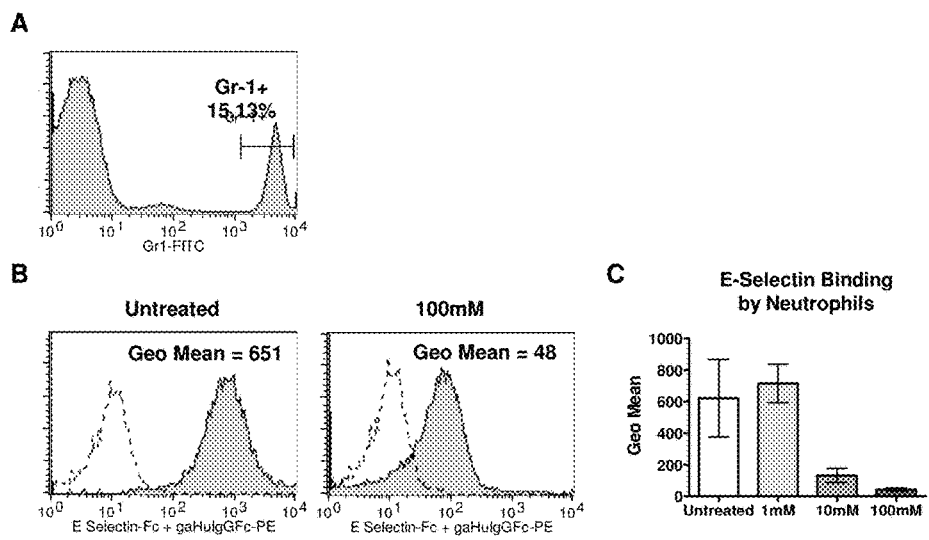
FIG. 6 shows the effects of administration of 2-fluorofucose on E-selectin binding to neutrophils. Panel A. An example of neutrophil identification by flow cytometry. Cells were gated on forward and side scatter to include live white blood cells and then applied to the histogram depicting Gr-1 staining to identify neutrophils. The positive cells were gated, the percentage positive cells determined (used for cell counts in FIG. 5B), and the gate was applied to the histograms in (B). Panel B. Examples of E-selectin binding to neutrophils from an untreated animal (left) and an animal treated with orally administered 2-fluorofucose (SGD-2083) at 100 mM (right). Grey histograms show E-selectin binding and the dotted lines show binding of the secondary reagent alone. The geometric mean fluorescent intensity was determined for E-selectin binding. Panel C. Geometric mean fluorescent intensity of E-selectin binding was determined for each animal as in (B) and compared between groups (n=3, per group; error bars represent standard deviation).

Oral administration of 2-fluorofucose also results in decreased in E-selectin binding to neutrophils (FIG. 6). The effects of the fucoses analogs was also dose-dependent, with 1 mM having little effect and 10 mM and 100 mM having increasing effects (FIGS. 5B and 5C).

The observed increases in circulating white blood cells and neutrophils (leukocytosis) is consistent with the inhibition of E-selectin binding by neutrophils. E-selectin mediates extravization of white blood cells into the periphery and lymph nodes, and inhibition of E-selectin binding (by inhibiting fucosylation) would also reduce extravization and result in accumulation of white blood cells in the blood. These results suggest that fucose analogs that inhibit protein fucosylation, and E-selecin fucosylation in particular, can act to inhibit autoimmunity.

Example 7

Tumor Growth Inhibition by Administration of Fucose Analogs

Study 1

Human-derived cell lines were evaluated for their susceptibility to the fucose analog 2-fluorofucose in vitro. The cells lines were: LS174T colon adenocarcinoma, PC-3 colon adenocarcinoma, HL-60 acute mylogenous leukemia, Ramos Burkitt lymphoma, and Caki-1 renal cell carcinoma. The cell lines were cultured in the presence of 100 μM 2-fluorofucose (SGD-2083) in growth media, 100 μM alkynylfucose (SGD-1887) in growth media, or control growth media (without a fucose analog) for two weeks. The growth media were MEM Eagle with 10% FBS (LS174T), 50:50 F12 and RPMI with 10% FBS (PC-3), RPMI with 10% FBS (HL-60), IMDM with 10% FBS (Ramos), and McCoy with 10% 1-BS (PC-3). The cells were evaluated for cell surface fucosylation by FACS using antibody cBR96 to detect LewisY, antibody SSEA-1 to detect LewisX, P-selectin ligand to detect P-selectin, and AOL lectin to detect the general level of fucosylation.
Results:

The results of the FACS evaluation revealed variable levels of fucosylated cell surface proteins on the different cell lines (data not shown). 2-fluorofucose (SGD-2083) was generally a better inhibitor of protein fucosylation than alkynyl fucose (SGD-1887).

Study 2

To further evaluate the activity of these fucose analogs, further studies were performed in vivo using tumor cells that had been pre-treated by culturing in the presence of a fucose analog, or using untreated tumor cells. Tumor cells were implanted into 10 mice per group as follows. For the LS174T, PC-3, and Caki-1 cell lines, $5 \times 10^5$ cells in 25% Matrigel were implanted subcutaneously into female nude mice. For HL-60 and Ramos cell lines, $5 \times 10^6$ cells were implanted subcutaneously into female SCID mice. For mice implanted with untreated tumor cells, mice were provided regular drinking water. For mice implanted with tumor cells pre-treated with 2-fluorofucose (SGD-2083), the mice were provided drinking water supplemented with 20 mM 2-fluorofucose (SGD-2083). For mice implanted with tumor cells pre-treated with alkylnyl fucose (SGD-1887), the mice were provided with regular drinking water. The mice did not drink water containing alkynyl fucose.

After 3 weeks of receiving 2-fluorofucose-containing drinking water, mice were returned to regular drinking water, except for mice with Caki-1 tumors. The latter mice were returned to regular drinking water for one week. After the week of receiving regular water, mice were randomized to two groups of 5 each to receive drinking water supplemented with 20 mM 2-fluorofucose or regular drinking water. Mice were sacrificed when tumors reached about 1000 mm³.

Referring to FIG. 8A-E, tumor growth inhibition in vivo was seen for LS174T, PC-3, and Caki-1 cells treated with 2-flurofucose (SGD-2083). No change in tumor growth was observed for HL-60 and Ramos cells. For Caki-1, tumor growth inhibition was not observed during the first treatment period, but was observed after the mice were returned to 2-fluorofucose treatment. For the other cell lines, tumor growth inhibition appeared to start when tumor size had reached about 150 mm³. The slower growing Caki-1 tumors did not reach this point until the second treatment period with 2-fluorofucose (SGD-2083). These results indicate that treatment with fucose analogs can inhibit tumor growth.

Study 3

In a third study, tumor cells were implanted without prior treatment with a fucose analog. LS174T colon adenocarcinoma cells ($5 \times 10^5$ cells in 25% Matrigel) were implanted subcutaneously into female nude mice. Mice were supplied with 50 mM 2-fluorofucose (SGD-2083) in their drinking water from 7 days before implant until 21 days after implant, or were supplied with regular drinking water.

Results

Figure 8:
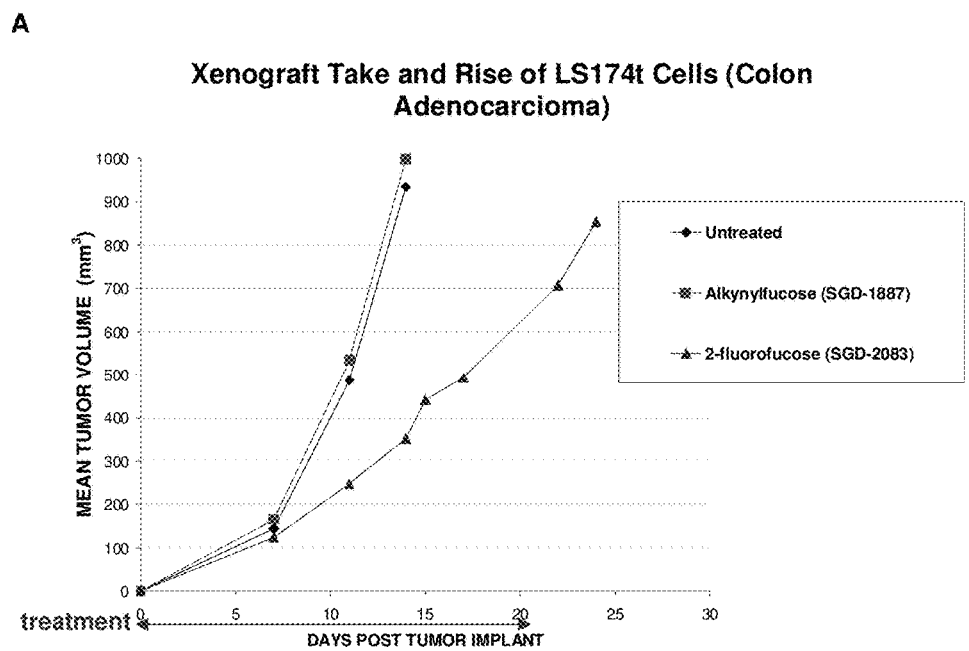
FIG. 8 shows the effects of administration of fucose analogs to mouse xenograft cancer models. The results of mouse xenograft models with L5174T, PC-3, Ramos, HL-60 and Caki-1 cell lines (pre-treated with 2-flurofucose (SGD-2083)), are shown in panels A-E, respectively. The results of a mouse xenograft model with an untreated LS174Tcell lines are shown in panel F.
Figure 8:
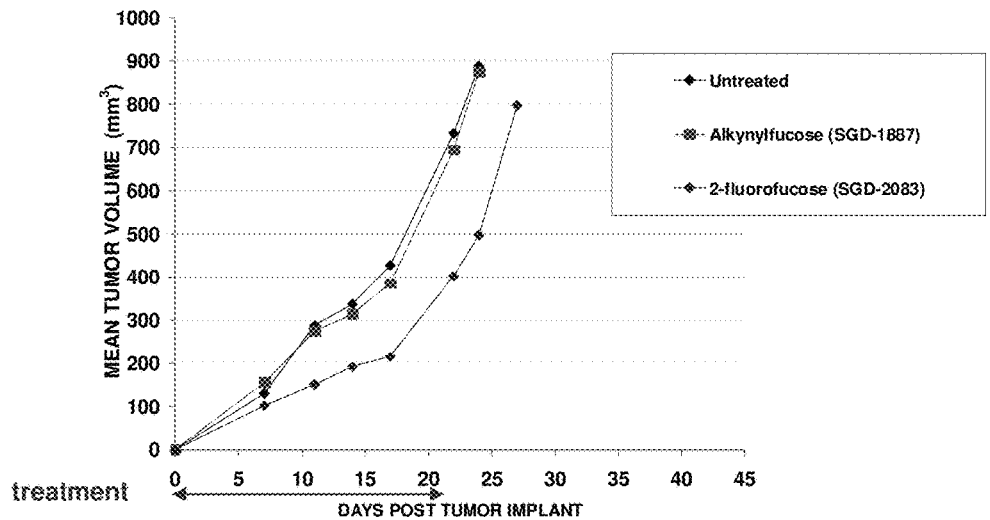
Figure 8:
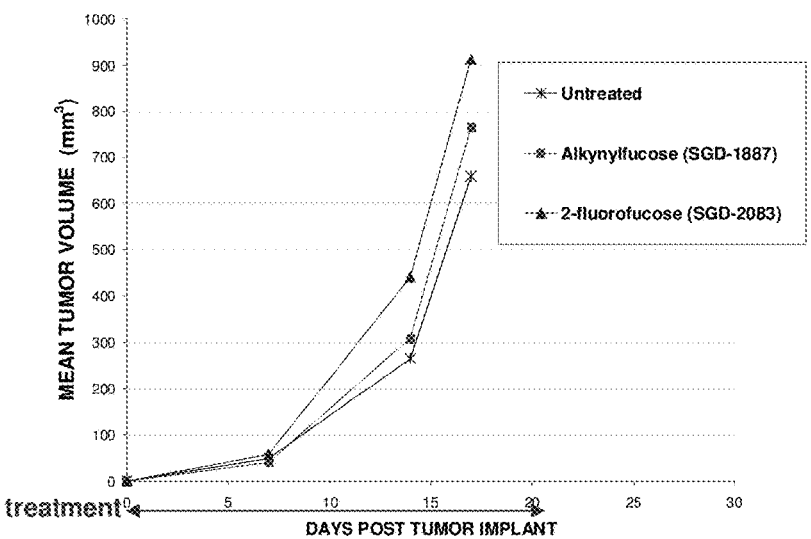
Figure 8:
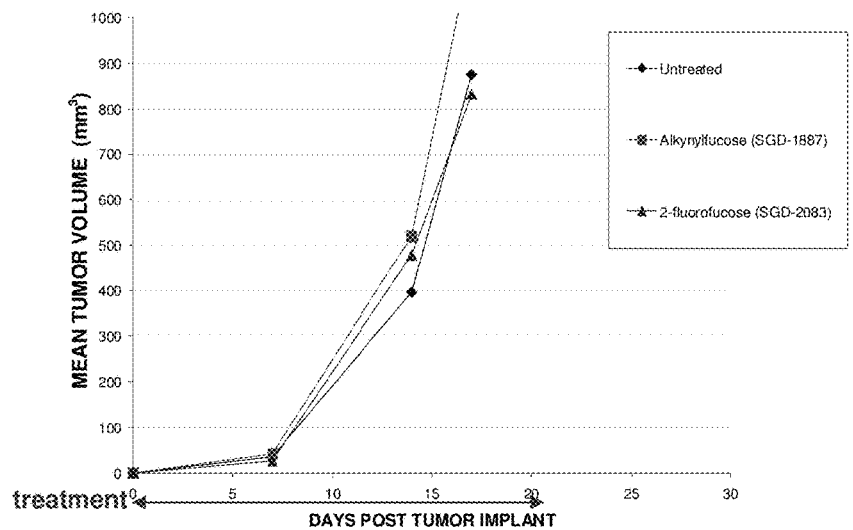
Figure 8:
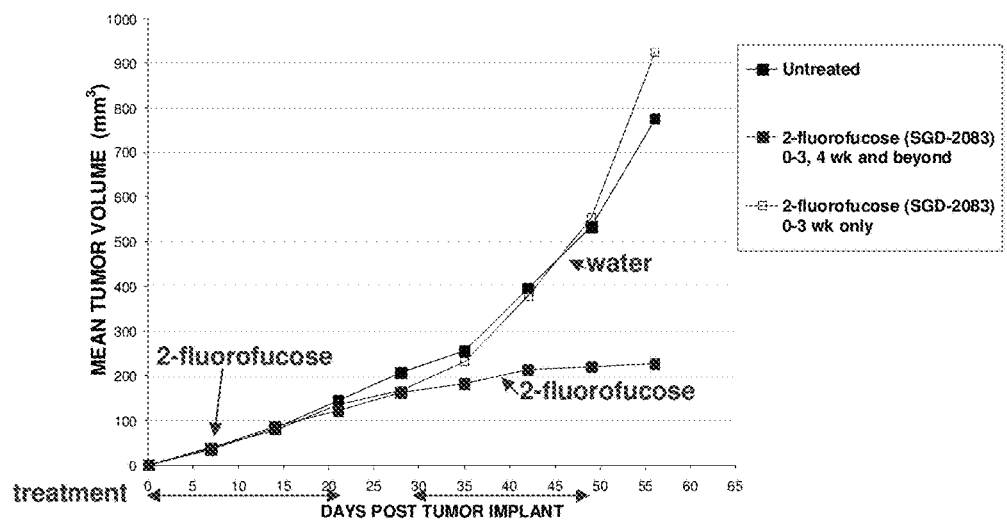
Figure 8:
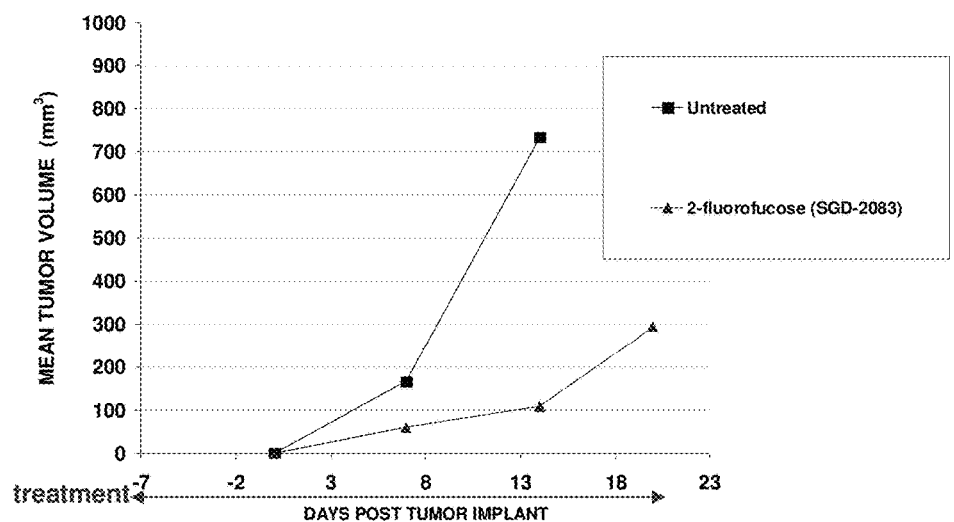

Referring to FIG. 8F, Mice given 50 mM 2-fluorofucose (SGD-2083) in their drinking water showed a substantial inhibition of tumor growth, achieving an average tumor size of 110 mm³ versus 734 mm³ for mice supplied with regular drinking water. Collectively, these results suggest that administration of a fucose analog can inhibit tumor growth.

Example 8

Tumor Vaccine Model

Figure 9:
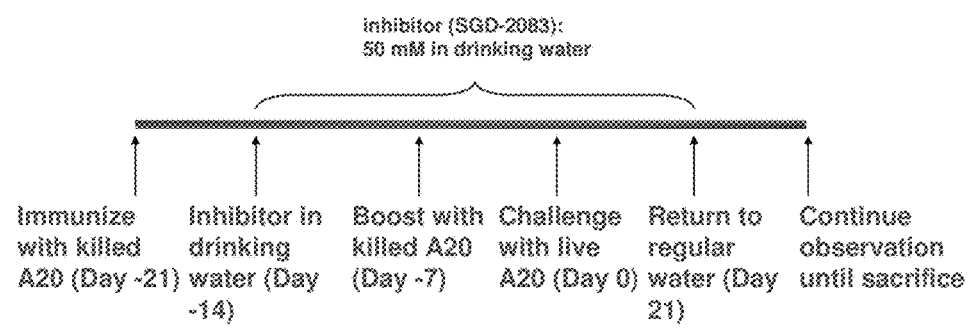
FIG. 9 shows the study design (panel A) and results (panel B) of a tumor vaccine model based on preimmunization with killed A20 murine lymphoma cells, followed by challenge with live A20 cells with or without administration of a fucose analog, (2-fluorofucose).
Figure 9:
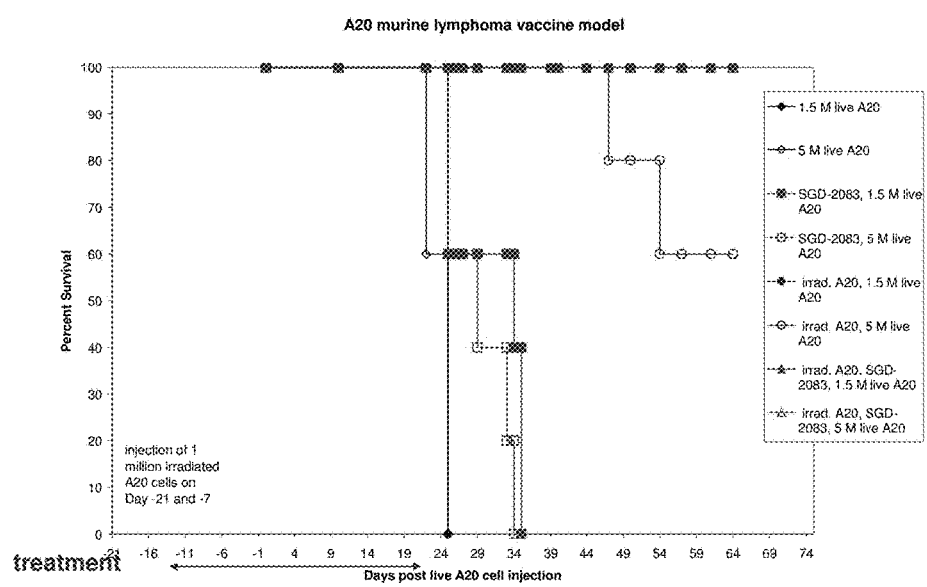

Female Balb/c mice were immunized by subcutaneous implantation of 1 million A20 murine lymphoma cells (killed by irradiation) on day −21 and day −7. Another group of mice were not given any immunization. On day 0, all mice were inoculated iv with 1.5 or 5 million live A20 cells. On days −14 through +21, mice were provided with 50 mM 2-fluorofucose (SGD-2083) in their drinking water or given regular drinking water. The 8 treatment groups were as follows:

1. No immunization, 1.5 million live A20 cells, regular drinking water
2. No immunization, 5 million live A20 cells, regular drinking water
3. No immunization, 1.5 million live A20 cells, 50 mM SGD-2083 in drinking water
4. No immunization, 5 million live A20 cells, 50 mM SGD-2083 in drinking water
5. Immunized, 1.5 million live A20 cells, regular drinking water
6. Immunized, 5 million live A20 cells, regular drinking water
7. Immunized, 1.5 million live A20 cells, 50 mM SGD-2083 in drinking water
8. Immunized, 5 million live A20 cells, 50 mM SGD-2083 in drinking water Results Referring to FIG. 9A, the study design is shown. Referring to FIG. 9B, mice that did not receive any immunization succumbed to the live A20 challenge from days 22-35. Mice receiving 2-fluorofucse (SGD-2083) survived a few days longer than those receiving regular drinking water. Two mice immunized with 5 million killed A20 cells and receiving regular drinking water succumbed to the live A20 challenge. All mice receiving immunization and 2-fluorofucose (SGD-2083) in their drinking water were still alive at data collection.

The present invention is not limited in scope by the specific embodiments described herein. Various modifications of the invention in addition to those described herein will become apparent to those skilled in the art from the foregoing description and accompanying figures. Such modifications are intended to fall within the scope of the appended claims. Unless otherwise apparent from the context any step, element, embodiment, feature or aspect of the invention can be used in combination with any other. All patent filings, and scientific publications, accession numbers and the like referred to in this application are hereby incorporated by reference in their entirety for all purposes to the same extent as if so individually denoted.

What is claimed is:

1. A method for the treatment of cancer having protein fucosylation in a human in need thereof, comprising administering to the human a therapeutically effective amount of a fucose analog or a biologically acceptable salt thereof, or a composition thereof, wherein each fucose analog has formulae (III) or (IV):

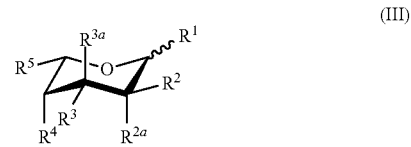

-continued

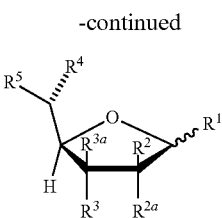
(IV)

wherein each fucose analog of formula (III) or (IV) can be the alpha or beta anomer or the corresponding aldose form;
wherein each of $R^1$, $R^3$, and $R^4$ is independently selected from the group consisting of —OH and —OC(O)$C_1$-$C_{10}$ alkyl, $R^2$ is F, $R^{2a}$ and $R^{3a}$ are each H, and $R^5$ is —$CH_3$.

2. The method of claim 1, wherein each of $R^1$, $R^3$, and $R^4$ is independently selected from the group consisting of —OH and —OAc, $R^2$ is F, $R^{2a}$ and $R^{3a}$ are each H, and $R^5$ is —$CH_3$.

3. The method of claim 1 wherein the fucose analog is 2-deoxy-2-fluorofucose.

4. The method of claim 1 wherein the fucose analog is 2-deoxy-2-fluorofucose peracetate.

5. The method of claim 1 further comprising administering a tumor-associated antigen or an antigenic fragment thereof as an immunogen.

6. The method of claim 1 further comprising administering a chemotherapeutic agent.

7. The method of claim 1 wherein administration is oral administration.

8. The method of claim 1 wherein administration of the therapeutically effective amount is in the form of one or more dosage units.

9. The method of claim 1 wherein protein fucosylation in the human is reduced by at least 10% relative to the amount of protein fucosylation in the absence of administration of said fucose analog.

10. The method of claim 9 wherein protein fucosylation in the human is reduced by about 20% relative to the amount of protein fucosylation in the absence of administration of said fucose analog and wherein the mammal is a human.

11. The method of claim 9 wherein protein fucosylation in the human is reduced by about 30% relative to the amount of protein fucosylation in the absence of administration of said fucose analog.

12. The method of claim 9 wherein protein fucosylation in the human is reduced by about 40% relative to the amount of protein fucosylation in the absence of administration of said fucose analog.

13. The method of claim 9 wherein protein fucosylation in the human is reduced by about 50% relative to the amount of protein fucosylation in the absence of administration of said fucose analog.

14. The method of claim 9 wherein protein fucosylation in the human is reduced by about 60% relative to the amount of protein fucosylation in the absence of administration of said fucose analog.

15. The method of claim 1 wherein fucosylation of white blood cells in the serum of the human is reduced by at least about 10% relative to the amount of fucosylation of white blood cells in the serum of a mammal in the absence of administration of said fucose analog.

16. The method of claim 15 wherein fucosylation of white blood cells in the serum of the human is reduced by at least about 20% relative to the amount of fucosylation of white blood cells in the serum of a mammal in the absence of administration of said fucose analog.

17. The method of claim 16 wherein fucosylation of white blood cells in the serum of the human is reduced by at least about 60% relative to the amount of fucosylation of white blood cells in the serum of a mammal in the absence of administration of said fucose analog.

18. The method of claim 1 wherein the cancer is a hematologic malignancy.

19. The method of claim 18 wherein the hematologic malignancy is lymphoma.

20. The method of claim 18 wherein the hematologic malignancy is leukemia.

* * * * *